(12) United States Patent
Kawasaki et al.

(10) Patent No.: US 6,924,132 B1
(45) Date of Patent: Aug. 2, 2005

(54) PROTEIN COMPLEMENTING YEAST LOW TEMPERATURE-SENSITIVITY FERMENTABILITY

(75) Inventors: Hideki Kawasaki, Tsuchiura (JP); Masaya Tokai, Setagaya-ku (JP); Yasuhiro Kikuchi, Tsukuba (JP); Kozo Ouchi, Hasuda (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 740 days.

(21) Appl. No.: 09/678,023

(22) Filed: Oct. 4, 2000

Related U.S. Application Data

(62) Division of application No. 08/894,344, filed as application No. PCT/JP96/03862 on Dec. 27, 1996, now Pat. No. 6,172,196.

(30) Foreign Application Priority Data

Dec. 28, 1995 (JP) ............................................... 7/343700

(51) Int. Cl.$^7$ .............................. C12P 7/06; C12N 1/14; A21D 10/00; C07H 21/04; C07K 1/00
(52) U.S. Cl. ........................ 435/161; 426/549; 426/60; 435/254.21; 536/23.7; 530/350
(58) Field of Search ........................... 435/254.21, 161; 530/350; 536/23.7; 426/549

(56) References Cited

U.S. PATENT DOCUMENTS 5,399,492 A    3/1995    Gysler et al. ............. 435/172.1

FOREIGN PATENT DOCUMENTS

| EP | 0667099 | 8/1995 |
|---|---|---|
| JP | 07-79767 | 3/1995 |
| JP | 07-213277 | 8/1995 |
| WO | WO 01724 | 2/1993 |

OTHER PUBLICATIONS

Appl. Environ, Microbiol., vol. 61, No. 2 (1995), pp. 639–642.
The 23$^{rd}$ European Brewery Conv. Proc. (1991), pp. 297–304.
Current Genetics, vol. 20 (1991), pp. 453–456.
Current Genetics, vol. 13 (1988), pp. 461–469.
Proc. Nat'l. Acad. Sci., vol. 93 (1996), pp. 5301–5306.
J. Bacteriol., vol. 156, No. 3 (1983), pp. 1363–1365.
A. Hino, et al, "New Freeze–Tolerant Yeast for Frozen Dough Preparations", Cereal Chemistry, vol. 64, No. 4, 1987, pp. 269–275.
Database EMBL 'Online!, "*Saccharomyces cerevisiae* Chromosome XXII Cosmid 9449," SCL9449, Apr. 10, 1996, XP002176984.
Database EMBL 'Online!, "*S. cerevisiae* Chromosome XII Reading Frame ORF YLR087c", SCYLR087C, May 28, 1996, XP002176983.
M. Tokai et al., "Cloning and Characterization of the *CSF1* Gene of *Saccharomyces cerevisiae*, Which is Required for Nutrient Uptake at Low Temperature", Jour. Bacteriology, vol. 182, No. 10, May 2000, pp. 2865–2868.

*Primary Examiner*—Rebecca E. Prouty
*Assistant Examiner*—Malgorzata A. Walicka
(74) *Attorney, Agent, or Firm*—Fitzpatrick, Cella, Harper & Scinto

(57) ABSTRACT

The present invention relates to yeast having DNA encoding a protein having the amino acid sequence of SEQ ID NO:2, or a gene which comprises DNA having the nucleotide sequence of SEQ ID NO: 1.

11 Claims, 2 Drawing Sheets

PROTEIN COMPLEMENTING YEAST LOW TEMPERATURE-SENSITIVITY FERMENTABILITY

This application is a division of application Ser. No. 08/894,344, filed Aug. 15, 1997, now U.S. Pat. No. 6,172,196 issued Jan. 9, 2001, which is a 371 of PCT/JP96/03862, Dec. 27, 1996.

TECHNICAL FIELD

The present invention relates to a process for making bread with refrigerated dough and a process for producing ethanol.

BACKGROUND ART

Recently, in the bread manufacturing industry, a method for making bread with refrigerated dough has been widely used with the purpose of saving labor in the bread making process and meeting diverse needs of consumers. In this method, partially fermented dough is stored at a low temperature in a refrigerator and then is subjected to fermentation, proofing and baking to make bread. Such a method is usually carried out by the use of refrigeration-resistant yeast, that is, yeast which is capable of controlling fermentation during the storage of dough at a low temperature and allowing normal fermentation at temperatures for fermentation and proofing to raise the dough.

As for the breeding of refrigeration-resistant yeast, there are known methods in which yeast strains of wild type are conferred with the mutation exhibiting low-temperature-sensitive fermentability by artificial mutagenesis [e.g., Japanese Published Examined Patent Application No. 71474/95, Japanese Published Unexamined Patent Application No. 213277/95, Japanese Published Unexamined Patent Application No. 79767/95, and Appl. Environ. Microbiol., 61, 639–642 (1995)]. The yeast strains conferred with the mutation exhibiting low-temperature-sensitive fermentability are used as refrigeration-resistant yeast or as parent strains for breeding refrigeration-resistant yeast.

However, such mutagenesis induces mutation at random and thus may possibly confer the yeast with mutation relating to the basic properties of fermentation such as dough raising, in addition to the low-temperature-sensitivity mutation.

It is also known to confer baker's yeast or brewer's yeast with favorable properties such as flocoulation [The 23rd European Brewery Conv. Proc., 297–304 (1991)] and flavor [Curr. Genet., 20, 453–456 (1991)] by using gene manipulation techniques.

However, a gene relating to the low-temperature-sensitivity of fermentability or a method for breeding refrigeration-resistant yeast by gene manipulation is not known.

Ethanol is produced by fermentation of sugar materials (e.g. molasses) or starch materials (e.g. corn and potato) as carbon sources. Fermentation can be generally carried out at a temperature of 30 to 43° C. Usually, the fermentation temperature is adjusted to 30 to 35° C. by cooling in order to avoid the death, insufficient growth, or decrease in fermentability of yeast caused by the rise of temperature. However, in the summer months, cooling is often insufficient, thereby causing the rise of culturing temperature to 35 to 38° C. in the course of alcohol fermentation. Thus, alcohol fermentation is usually carried out with further cooling to prevent the rise of temperature due to fermentation heat. A need exists for temperature-resistant yeast which is useful for saving cost for cooling in such process.

As for the breeding of thermotolerant yeast, there have been reports on a method in which mitochondria relating to thermotolerance is introduced [Juan Jimenez, et al.: Curr. Genet., 13, 461–469 (1988)] and a method in which heat shock protein HSP104 is expressed at a high level [Susan Lindquist, et al.: Proc. Natl. Acad. Sci. USA, 93, 5301–5306 (1996)]. However, application of these methods to alcohol fermentation has not been studied. Further, it is known that the heat-resistance of yeast is improved by heat treatment at temperatures which are not fatal to the yeast [B. G. Hall: J. Bacteriol., 156, 1363 (1983)], but this effect is not lasting, and it is difficult to apply this method to alcohol fermentation.

DISCLOSURE OF THE INVENTION

The present invention relates to a protein having the amino acid sequence encoded by SEQ ID NO: 1, or a protein capable of complementing the mutation exhibiting low-temperature-sensitive fermentability and having an amino acid sequence wherein one or more amino acid residues are added, deleted or substituted in the amino acid sequence encoded by SEQ ID NO: 1; a gene which encodes said protein; and a gene which comprises DNA having the nucleotide sequence of SEQ ID NO: 1, or comprises DNA capable of complementing the mutation exhibiting low-temperature-sensitive fermentability and having a nucleotide sequence wherein one or more nucleotides are added, deleted or substituted in the nucleotide sequence of SEQ ID NO: 1. The present invention also relates to yeast belonging to the genus *Saccharomyces* and having low-temperature-sensitive fermentability which is characterized in that the above-mentioned gene on the chromosome is inactivated; dough containing said yeast; a process for making bread which comprises adding said yeast to dough; and a process for producing ethanol which comprises culturing said yeast in a medium, allowing ethanol to accumulate in the culture, and recovering ethanol from the culture.

The expression "having low-temperature-sensitive fermentability" as used herein means the property of having substantially no fermentability at temperatures for low temperature storage and having normal fermentability at temperatures for fermentation and proofing after the low temperature storage. For instance, in the case of baker's yeast, it means the property of having substantially no dough-raising ability at 5° C. and having normal dough-raising ability at 20 to 40° C. after the storage under refrigeration at 5° C. for 1 to 7 days, and in the case of brewer's yeast, it means the property of having substantially no alcohol fermentability at 5° C. and having normal alcohol fermentability at 20 to 40° C. after the storage under refrigeration at 5° C. for 1 to 7 days.

Isolation of a gene which complements the mutation exhibiting low-temperature-sensitive fermentability, determination of the DNA sequence of said gene, and inactivation of said gene can be carried out by using basic techniques for genetic engineering and biological engineering according to the descriptions in commercially available experiment manuals, e.g. Gene Manual, Kodansha Co., Ltd.; Methods for Experiments in Gene Manipulation, edited by Yasutaka Takagi, Kodansha Co., Ltd.; Molecular Cloning, Cold Spring Harbor Laboratory (1982); Molecular Cloning, 2nd ed., Cold Spring Harbor Laboratory (1989); Methods in Enzymology, 194 (1991); and Gene Experiments Using Yeasts (an extra number of Experimental Medicine), Yodosha Co., Ltd. (1994).

The gene which complements the mutation exhibiting low-temperature-sensitive fermentability according to the present invention (hereinafter referred to as the gene complementing low-temperature-sensitivity) can be isolated, for example, as the gene complementing the low-temperature-sensitivity of fermentability of *Saccharomvces cerevisiae* RZT-3 (FERM BP-3871) (hereinafter referred to as RZT-3 strain) described in Japanese Published Unexamined Patent Application No. 336872/93. That is, the gene complementing low-temperature-sensitivity can be isolated by transforming RZT-3 strain with the DNA library of the yeast carrying the gene complementing low-temperature-sensitivity, and obtaining DNA from the strain of which the mutation exhibiting low-temperature-sensitive fermentability is complemented.

The DNA library of the yeast carrying the gene complementing low-temperature-sensitivity can be prepared by cleaving the chromosomal DNA of yeast carrying a gene of wild type, e.g. *Saccharomyces cerevisiae* X2180-1B (hereinafter referred to as X2180-1B strain) with a restriction enzyme, and ligating each of the obtained DNA fragments with a vector capable of being maintained in yeast.

Any restriction enzymes which can cleave the chromosomal DNA can be used in the above process. Preferably, those which give DNA fragments of 20 Kbp or less are used. The chromosomal DNA may be completely digested or partially digested with the restriction enzyme.

Examples of the vectors capable of being maintained in yeast are YCp vectors, YEp vectors, YRp vectors, YIp vectors, and YAC (yeast artificial chromosome) vectors.

The transformation of RZT-3 strain with the DNA library can be carried out according to the methods generally used in genetic engineering and biological engineering such as the spheroplast method [e.g. Proc. Natl. Acad. Sci. USA, 75, 1929–1933 (1978)], the lithium acetate method [e.g. J. Bacteriol, 153, 163–168 (1983)], and the electroporation method [e.g. Methods in Enzymology, 194, 182–187 (1991)].

The complementation of the mutation exhibiting low-temperature-sensitive fermentability can be confirmed by examining the transformed yeast for the growth at a low temperature or the fermentability at a low temperature [Appl. Environ. Microbiol., 61, 639–642 (1995)]. The examination on fermentability at a low temperature can be carried out, for example, by the pigment agar layer method described below. In this method, the test strain is cultured at 30° C. on YPG agar medium (1% yeast extract, 2% peptone, 3% glycerol, and 2% agar) to form colonies. Then, a pigment agar (0.5% yeast extract, 1% peptone, 10% sucrose, 0.02% Bromocresol Purple, and 1% agar, pH 7.5) is layered over the medium, and the plate is kept at a low temperature (e.g. 5° C.). Bromocresol Purple is a pH indicator, and the pigment agar assumes a purple color when being layered. Fermentation of the yeast lowers the pH of the medium around the colony, thereby causing the change of the color of that area from purple to yellow. Accordingly, a strain showing the color change to yellow around the colony while the layered plate is kept at a low temperature can be selected as a strain having fermentability at a low temperature.

Recovery of a plasmid from the yeast and transformation of *Escherichia coli* using the plasmid can be carried out according to the methods generally used in genetic engineering. For example, the plasmid can be recovered by the method described in Gene Experiments Using Yeasts (an extra number of Experimental Medicine), Yodosha Co., Ltd. (1994), and the transformation can be carried out by the method described in Molecular Cloning, 2nd ed., Cold Spring Harbor Laboratory (1989).

The nucleotide sequence of the gene complementing low-temperature-sensitivity can be determined by the methods generally used in genetic engineering such as the Maxam-Gilbert method and the dideoxy method.

The polypeptide encoded by the gene complementing low-temperature-sensitivity can be readily obtained by using current knowledge of molecular genetics. If necessary, analysis using computers can be made [e.g. Cell Technology, 14, 577–588 (1995)]. It is possible to use the polypeptide encoded by the gene complementing low-temperature-sensitivity as an inhibitor to the low-temperature-sensitivity of fermentability in the yeast having low-temperature-sensitive fermentability.

The present invention has clarified the nucleotide sequence of the gene complementing low-temperature-sensitivity and the amino acid sequence of the polypeptide encoded by the gene, and thereby has enabled disruption of the gene complementing low-temperature-sensitivity, regulation of expression or alteration of expression level of the gene complementing low-temperature-sensitivity by modification of the promoter, expression of various genes by the use of the promoter of the gene complementing low-temperature-sensitivity, preparation of a fused gene in which the gene complementing low-temperature-sensitivity is fused with another gene as well as a fused polypeptide, and the like. These manipulations can be carried out by using, for example, the methods described in Methods in Enzymology, 194, 594–597 (1991).

The methods for inactivating the gene complementing low-temperature-sensitivity in yeast are described below.

The term inactivation of the gene as used herein refers to the lowering or loss of functions inherent in the gene or the polypeptide encoded by the gene induced by various techniques for genetic engineering or biological engineering; for example, gene disruption [e.g. Methods in Enzymology, 194, 281–301 (1991)], introduction of a movable genetic element into the gene [e.g. Methods in Enzymology, 194, 342–361 (1991)], introduction and expression of the antisense gene [e.g. Japanese Published Examined Patent Application No. 40943/95, and The 23rd European Brewery Conv. Proc., 297–304 (1991)], introduction of DNA relating to silencing to the vicinity of the gene [e.g. Cell, 75, 531–541 (1993)], and treatment of the polypeptide encoded by the gene with an antibody [e.g. European J. Biochem., 231, 329–336 (1995)].

For the inactivation of the gene complementing low-temperature-sensitivity, any yeast which belongs to the genus *Saccharomyces*, preferably *Saccharomyces cerevisiae*, can be used. That is, various kinds of yeasts such as baker's yeast, sake yeast, wine yeast, beer yeast, miso and soy sauce yeast, and ethanol-producing yeast belonging to the genus *Saccharomyces* can be used.

The disruption of the gene complementing low-temperature-sensitivity means a process which comprises introducing into yeast cells DNA which has a nucleotide sequence homologous to that of the gene complementing low-temperature-sensitivity but is incapable of acting as the gene complementing low-temperature-sensitivity due to a mutation such as addition, deletion or substitution, to induce homologous recombination, and thereby incorporating this mutation into the gene on the genome.

The DNA used for the gene disruption can be prepared, for example, by a method which comprises cleavage of the gene complementing low-temperature-sensitivity with restriction enzymes to add, delete or substitute nucleotides, and a method which comprises extracellular mutation (in vitro mutagenesis) of the gene complementing low-temperature-sensitivity. For the addition and substitution of nucleotides, a method can be used in which the marker gene is inserted.

The disruption of the gene complementing low-temperature-sensitivity can be effected by disruption of any of the promoter region, open reading frame region, and terminator region of the gene, or combinations of such regions. The gene complementing low-temperature-sensitivity can also be disrupted by deleting the entire gene.

The disruption of the gene complementing low-temperature-sensitivity can be carried out, for example, by transforming yeast with a plasmid for the disruption of the gene complementing low-temperature-sensitivity of the yeast or a fragment of the plasmid to induce homologous recombination of a DNA fragment carried on the transforming plasmid or its fragment with the gene on the genome of the yeast. The plasmid for the disruption of the gene complementing low-temperature-sensitivity or its fragment must have homology to the gene complementing low-temperature-sensitivity on the genome of the yeast in a degree sufficient for the induction of homologous recombination. A DNA fragment can be examined for the capability of inducing homologous recombination by introducing the DNA fragment into yeast, and then examining whether a strain carrying homologous recombination, that is, a strain having low-temperature-sensitive fermentability can be isolated.

Suitable vectors to be used for the construction of the plasmid for the disruption of the gene complementing low-temperature-sensitivity include vectors capable of being maintained in yeast as well as vectors capable of being maintained in *Escherichia coli* such as pUC19, pBR322, and BluscriptII SK$^+$.

As the marker gene, any marker genes which can be used in yeast are usable. Examples of suitable genes are genes complementing auxotrophic mutation such as URA3, TRP1, LEU2, and HIS3, and genes relating to resistance to chemicals such as G418, hygromycin B, cerulenin, and parafluorophenylalanine [e.g. J. Ferment. Bioeng., 76, 60–63 (1993), and Enzyme and Microb. Technol., 15, 874–876 (1993)].

The gene complementing low-temperature-sensitivity on the genome of yeast can be disrupted by transforming the yeast with the plasmid for the disruption of the gene complementing low-temperature-sensitivity.

The transformation of the yeast can be carried out according to the methods generally used in genetic engineering and biological engineering such as the spheroplast method, the lithium acetate method, and the electroporation method mentioned above.

Introduction of the marker gene into the plasmid for the disruption of the gene complementing low-temperature-sensitivity enables ready isolation of a transformant by using the marker as an indicator. The transformant can also be isolated based on the exhibition of low-temperature-sensitive fermentability, which is an indication of the disruption of the gene complementing low-temperature-sensitivity on the genome of the yeast. The low-temperature-sensitivity of the strain of which the gene complementing low-temperature-sensitivity has been disrupted can be confirmed by examining the yeast for the growth or fermentability at a low temperature.

By the above-described process, yeast having low-temperature-sensitive fermentability which is characterized in that the gene complementing low-temperature-sensitivity is inactivated can be obtained. An example of such yeast is *Saccharomyces cerevisiae* YHK1243 (hereinafter referred to as YHK1243 strain). This strain was deposited with the National Institute of Bioscience and Human-Technology, Agency of Industrial Science and Technology, Ministry of International Trade and Industry (1–3, Higashi 1-chome, Tsukuba-shi, Ibaraki-ken) on Dec. 7, 1995 with accession number FERM BP-5327 under the Budapest Treaty.

The following Test Examples show that the low-temperature-sensitivity of fermentability of YHK1243 strain is improved.

TEST EXAMPLE 1

Test on Low-temperature-sensitivity of Fermentability

One loopful of YHK1243 strain was inoculated into 5 ml of YPD medium comprising 1% yeast extract, 2% peptone and 2% glucose in a test tube, and cultured at 30° C. for 16 hours. The resulting culture (1 ml) was inoculated into 50 ml of YPD medium in a 300-ml Erlenmeyer flask, and cultured at 30° C. for 24 hours. After the completion of culturing, the cells were collected by centrifugation and washed twice with deionized water. The obtained wet cells (0.61 g) were suspended in 50 ml of a fermentation test medium [0.67% Yeast Nitrogen Base w/o Amino Acid (Difco Laboratories Inc.), 2% sucrose, and 1% sodium succinate (adjusted to pH 4.5 with concentrated hydrochloric acid)] in a test tube (inside diameter: 22 mm, height: 200 mm). A silicone stopper equipped with a silicone tube was put in the test tube, and culturing was carried out at 5° C. for 24 hours. The gas generated during the culturing was collected in a saturated aqueous solution of sodium chloride via the silicone tube, and the volume of the gas was measured to calculate the amount of carbon dioxide gas generated per gram of yeast cells. The same procedure as above was also carried out on YOY655 strain to calculate the amount of carbon dioxide gas generated per gram of cells.

The results are shown in Table 1.

TABLE 1

| Strain | Amount of Carbon Dioxide Gas (ml/g of cells*) |
|---|---|
| YOY655 strain | 133 |
| YHK1243 strain | 15 |

*Converted as yeast cells having a dry matter content of 27%

The amount of carbon dioxide gas generated by YHK1243 strain at 5° C. was approximately 1/9 of that by YOY655 strain.

TEST EXAMPLE 2

Test on Low-temperature-sensitivity of Fermentability (2)

One loopful of YHK1243 strain was inoculated into 30 ml of YPD medium in a 300-ml Erlenmeyer flask, and cultured at 30° C. for 24 hours. The whole of the resulting culture was inoculated into 270 ml of a molasses medium (3% molasses, 0.193% urea, 0.046% potassium dihydrogenphosphate, and 2 drops of defoaming agent) in a 2-l Erlenmeyer flask with baffles, and cultured at 30° C. for 24 hours. After the completion of culturing, the cells were collected by centrifugation and washed twice with deionized water, followed by dehydration on a clay plate. The same procedure as above was also carried out on YOY655 strain to obtain cells.

The obtained cells of YHK1243 strain and YOY655 strain were respectively used for preparing dough according to the following dough composition and steps.

|  | (weight: g) |
|---|---|
| Dough Composition: | |
| Hard flour | 100 |
| Sugar | 5 |
| Salt | 2 |
| Yeast cells (YHK1243 strain or YOY655 strain) | 3 |
| Water | 62 |
| Steps: | |
| Mixing (at 100 rpm for 2 minutes with National Complete Mixer) ↓ | |
| Dividing (the dough is divided into five equal parts; 34.4 g each) ↓ | |
| Storage under refrigeration (in a refrigerator at 5° C. for 7 days) ↓ | |
| Thawing (at 30° C. and 85% relative humidity for 30 minutes) ↓ | |
| Measurement of the amount of carbon dioxide gas generated at 30° C. in 2 hours with Fermograph (ATTO Co., Ltd.) | |

Each dough was stored under refrigeration, and then the amount of carbon dioxide gas generated at 30° C. was measured for evaluation of the refrigeration resistance of the dough.

The results are shown in Table 2.

TABLE 2

| | Amount of Carbon Dioxide Gas (ml) | |
|---|---|---|
| Strain | Before Storage under Refrigeration | After Storage under Refrigeration |
| YOY655 strain | 124 | 68 |
| YHK1243 strain | 120 | 101 |

The dough containing YHK1243 strain generated a large amount of carbon dioxide gas at 30° C. after the storage under refrigeration, compared with the dough containing YOY655 strain. Further, rising of the dough containing YOY655 strain was observed during the storage under refrigeration, whereas rising of the dough containing YHK1243 strain was not substantially observed.

The dough containing the yeast belonging to the genus *Saccharomyces* and having low-temperature-sensitive fermentability which is characterized in that the gene complementing low-temperature-sensitivity is inactivated (hereinafter referred to as the yeast of the present invention) is described below.

The dough containing the yeast of the present invention refers to the dough prepared by mixing flour or rye flour with the yeast of the present invention, salt, water, and if necessary, additional ingredients such as fats and oils, sugar, shortening, butter, skim milk, yeast food, and eggs, and kneading the mixture.

The refrigeration conditions for storing the dough containing the yeast of the present invention are as follows: at a temperature of −5 to 10° C., preferably 0 to 5° C., for 1 to 10 days, preferably 1 to 7 days.

The process for preparing the dough containing the yeast of the present invention and the process for making bread which comprises adding the yeast of the present invention to dough are described below.

Yeast cells which are suitable for use in bread-making can be obtained by culturing the yeast of the present invention in an ordinary medium containing carbon sources, nitrogen sources, inorganic substances, amino acids, vitamins, etc. at 27 to 32° C. under aerobic conditions, collecting the cultured cells, and washing the cells.

Examples of the carbon sources in the medium are glucose, sucrose, starch hydrolyzate, and molasses. Particularly preferred is blackstrap molasses.

Examples of the nitrogen sources are ammonia, ammonium chloride, ammonium sulfate, ammonium carbonate, ammonium acetate, urea, yeast extract, and corn steep liquor.

Examples of the inorganic substances are magnesium phosphate and potassium phosphate. An example of the amino acids is glutamic acid, and examples of the vitamins are pantothenic acid and thiamine.

Fed-batch culture is desirable as the culturing method.

After the completion of culturing, the yeast cells of the present invention are collected by centrifugation or the like. The collected cells are added to flour or rye flour together with salt, water, and if necessary, fats and oils, sugar, shortening, butter, skim milk, yeast food, eggs, etc., followed by mixing, to prepare the dough containing the yeast of the present invention.

Bread can be made according to ordinary methods using the dough obtained as above. There are two kinds of typical methods for making one-loaf bread, buns, etc.; that is, the straight dough method and the sponge-dough method. The former is a method in which all the ingredients are mixed at a time. The latter is a method in which at first a sponge is made by kneading a part of the flour with yeast and water, and then, after fermentation, the remaining ingredients are added to the sponge.

In the straight dough method, all the ingredients are mixed and kneaded, and the kneaded mixture is fermented at 5 to 30° C. The fermented dough is subjected to the following steps: dividing, benching, molding, proofing (35 to 42° C.), and baking (200 to 240° C.). In the sponge-dough method, about 70% of the whole flour to be used, yeast, and yeast food are mixed and kneaded with water. The kneaded mixture is fermented at 25 to 35° C. for 3 to 5 hours, and then mixed and kneaded with the remaining ingredients such as flour, water, and salt (dough mixing). The obtained dough is subjected to the following steps: dividing, benching, molding, proofing (35 to 42° C.), and baking (200 to 240° C.).

Danish pastries, croissants, etc. are made, for example, in the following manner.

Flour, salt, the yeast of the present invention, sugar, shortening, eggs, skim milk, and water are mixed and kneaded to prepare dough. Then, fat such as butter or margarine is folded into the dough, and rolling and folding are repeated to make multiple layers of the dough and the fat. This step of folding the fat is called "roll-in", which can be carried out by two methods. In one method, the temperature of the dough to be kneaded is lowered to about 15° C., and the dough is kneaded until the intended number of layers are made without cooling. In the other method, which is the so-called retarding method, cooling is repeated several times using a refrigerator or a freezer in the course of the roll-in step.

The obtained dough is subjected to the following steps: rolling, dividing, molding, proofing (30 to 39° C.), and baking (190 to 210° C.).

The process for producing ethanol is described below which comprises culturing the yeast of the present invention in a medium, allowing ethanol to accumulate in the culture, and recovering ethanol from the culture.

The production of ethanol by using the yeast of the present invention is carried out by a conventional method for culturing yeast. The microorganism to be used in the present invention may be immobilized on a gel carrier such as agar, sodium alginate, polyacrylamide, or carageenan.

As the medium for the production of ethanol according to the present invention, either a synthetic medium or a natural medium may be used insofar as it appropriately contains carbon sources, nitrogen sources, inorganic substances, and other nutrients as required.

As the carbon sources, fermentation materials containing at least sucrose should be used. Other carbon sources which can be assimilated by the microorganism used such as sugars (e.g. glucose, fructose, galactose, and maltose) may also be used. As the fermentation materials containing sucrose, any synthetic or natural fermentation materials containing sucrose can be used; examples of suitable materials are sugarcane juice, sugar beet juice, and blackstrap molasses which is obtained after crystallization of sucrose in the process of producing sugar from such juices.

Examples of the nitrogen sources include organic or inorganic nitrogen sources such as urea, ammonia, ammonium sulfate, and ammonium nitrate, and natural nitrogen sources such as corn steep liquor, peptone, meat extract, and yeast extract.

Examples of the inorganic salts are potassium phosphate, sodium phosphate, magnesium sulfate, manganese sulfate, ferrous sulfate, potassium chloride, and sodium chloride.

As the other nutrients, vitamins such as thiamine hydrochloride, p-aminobenzoic acid, folic acid, riboflavin, and inositol, etc. can be used.

Culturing is usually carried out under aerobic conditions, for example, by shaking culture or aeration stirring culture. The culturing temperature is 25 to 50° C., preferably 30 to 43° C., and the pH is maintained at 3 to 7, preferably 4 to 6 during the culturing. Usually, the culturing is completed in 1 to 10 days.

After the completion of culturing, ethanol can be recovered from the culture by ordinary methods such as distillation.

BEST MODE FOR CARRYING OUT THE INVENTION

EXAMPLE 1

Cloning of the Gene Complementing Low-temperature-sensitivity (1) Conferment of ura3 Mutation on RZT-3 Strain RZT-3 strain, which is a yeast strain having low-temperature-sensitive fermentability, was conferred with ura3 mutation as a marker for introducing a plasmid according to the method of Boeke, et al. [Mol. Gen. Genet., 197, 345–346 (1984)]. That is, one loopful of RZT-3 strain was inoculated into YPD medium and cultured overnight at 30° C. with shaking. The resulting culture (100 μl) was smeared on FOA plate [0.67% Yeast Nitrogen Base w/o Amino Acid (Difco Laboratories Inc.), 0.1% 5-fluoroorotic acid, 0.005% uracil, 2% glucose, and 2% agar], and cultured at 30° C. for 3 days. From the colonies formed by the culturing was selected a strain having uracil-requirement which is complemented by transformation with plasmid YCP50 carrying URA3 as a marker, and having low-temperature-sensitive fermentability. This strain was designated *Saccharomyces cerevisiae* RZT-3u (hereinafter referred to as RZT-3u strain).

(2) Cloning

The chromosomal DNA of X2180-1B strain (obtained from Yeast Genetic Stock Center) was partially digested with Sau3AI, and the obtained DNA fragments were inserted into the BamHI site of plasmid YCp50 to prepare the gene library. RZT-3u strain was transformed with the gene library, followed by selection of non-uracil-requiring transformants. The obtained transformants were cultured on YrG agar medium at 30° C. to form colonies. Then, a pigment agar was layered over the medium and culturing was carried out at 5° C. for 1 to 3 days. A strain showing the color change to yellow around the colony during the culturing at 5° C., that is, a strain of which the fermentation was observed at 5° C., was isolated as a strain of which the mutation exhibiting low-temperature-sensitive fermentability was complemented. From this strain was extracted recombinant plasmid pHK162.

Plasmid pHK162 was introduced into *Escherichia coli* JM109 strain to prepare *Escherichia coli* EHK162 strain. The obtained strain was deposited with the National Institute of Bioscience and Human-Technology, Agency of Industrial Science and Technology, Ministry of International Trade and Industry on Dec. 7, 1995 with accession number FERM BP-5328 under the Budapest Treaty.

(3) Complementation Test

Figure 1:
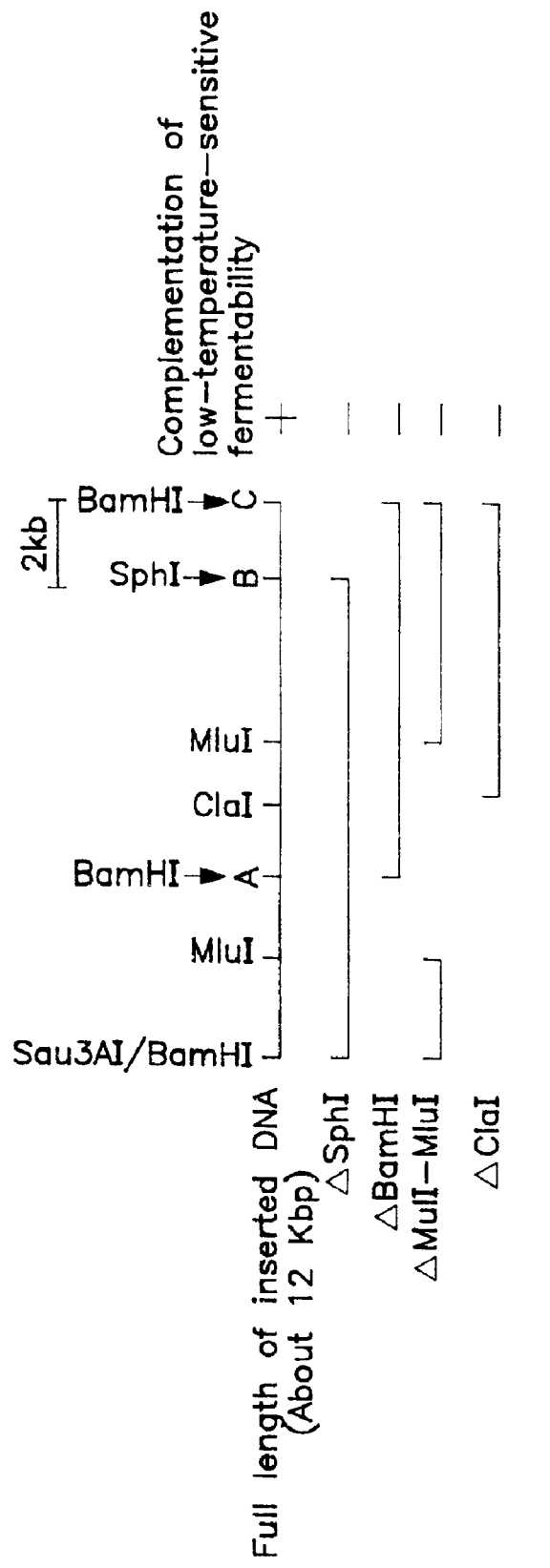
FIG. 1 shows the restriction map of the DNA fragment containing CSF1 gene and the results of the subcloning and complementation test carried out for the determination of the functional region of CSF1 gene.

Plasmid pHK162 carried an inserted Sau3AI/BamHI-BamHI fragment of about 12 Kbp. This plasmid was cleaved with various restriction enzymes and the obtained DNA fragments were separated by electrophoresis, followed by measurement of molecular weights, to prepare the restriction map as shown in FIG. 1. On the basis of this restriction map, recombinant plasmids were constructed by inserting each of the DNA fragments obtained by cleavage of the ca. 12 Kbp Sau3AI/3amHI-BamHI fragment with SphI, BamHI, MluI and ClaI into plasmid YCp50. The recombinant plasmids were used for transforming RZT-3u strain.

The obtained transformants were examined for complementation of the mutation exhibiting low-temperature-sensitive fermentability. As shown in FIG. 1, transformation of RZT-3u strain with plasmid pHK162 resulted in complementation of the mutation exhibiting low-temperature-sensitive fermentability, but transformation of the strain with the other recombinant plasmids did not complement the mutation exhibiting low-temperature-sensitive fermentability.

The above result shows that a DNA fragment which comprises the DNA fragment of about 6.5 Kbp from BamHI (A) (the sequence at positions 1291 through 1296 in the nucleotide sequence of SEQ ID NO: 1) to SphI (B) (the sequence at positions 7675 through 7680 in SEQ ID NO: 1) shown in FIG. 1 and additional sequences extending upstream of the 5' end and downstream of the 3' end of the BamHI-SphI fragment is necessary for complementing the mutation exhibiting low-temperature-sensitive fermentability of RZT-3u strain.

(4) Determination of Nucleotide Sequence

The nucleotide sequence of the 12 Kbp DNA fragment inserted into plasmid pHK162 was determined by the dideoxy method using a DNA sequencer (Pharmacia LKB, ALF DNA Sequencer II). As a result, a gene was found which comprises the region of about 6.5 Kbp cleaved at BamHI (A) and SphI (B) shown in FIG. 1 within the open reading frame. This gene was designated CSF1 gene. As shown in SEQ ID NO: 1, the polypeptide encoded by CSF1 gene which is presumed from the determined nucleotide sequence consists of 2958 amino acid residues (molecular weight: 338 kDa). DNA homology search with other genes revealed that the sequence of the upstream region in CSF1 gene comprising about 140 N-terminal amino acid residues in the open reading frame of CSF1 gene coincided with the sequence of the region located upstream of the sequence which was reported as the nucleotide sequence of GAA1 gene of *Saccharomyces cerevisiae* [Hamburger, et al.: J. Cell Biol., 129, 629–639 (1995)] (the region outside the GAA1 gene-encoding region). However, the report by Hamburger, et al. relates to GAA1 gene and contains no description about the presence of another gene (CSF1 gene) upstream from GAA1 gene. Further, in the nucleotide sequence reported by them, one base (T) is inserted between the base at position 198 (T) and the base at position 199 (G) in SEQ ID NO: 1. Thus, the polypeptide encoded by CSF1 gene is not anticipated by Hamburger, et al.

EXAMPLE 2

Preparation of Yeast Having Low-temperature-sensitive Fermentability (1) Construction of Plasmid for Gene Disruption About 5 μg of pHK162 plasmid DNA was dissolved in 20 μl of H buffer [50 mM Tris hydrochloride buffer (pH 7.5), 10 mM magnesium chloride, 1 mM dithiothreitol, and 100 mM sodium chloride], and 10 units of restriction enzyme BamHI was added thereto. Reaction was carried out at 30° C. for 3 hours, followed by separation of the reaction product by 0.8% agarose gel electrophoresis. The segment of the gel containing the band of the DNA fragment of about 8 kb from BamHI (A) to BamHI (C) shown in FIG. 1 was cut out, and the fragment was extracted and purified by using GENECLEAN II Kit (Bio 101 Co., Ltd.). The same procedure as above was repeated except that about 5 μg of pUC19 plasmid DNA was used in place of about 5 μg of pHK162 plasmid DNA, whereby a DNA fragment of about 2.8 kb was extracted and purified. The DNA fragment of about 8 kb derived from plasmid pHK162 (1 μg) and the DNA fragment of about 2.8 kb derived from plasmid pUC19 (0.1 μg) were subjected to ligation reaction overnight at 16° C. using Ligation Pack (Nippon Gene Co., Ltd.). The reaction mixture (2 μl) was used for transformation of competent high *E. coli* JM109 strain (Toyobo Co., Ltd.). The obtained transformant was smeared on 5-bromo-4-chloro-3-indolyl-β-D-galactoside (hereinafter referred to as X-gal) ampicillin LB agar medium and cultured at 37° C. for 20 hours. The X-gal ampicillin LB agar medium was prepared by dropping 50 μl of 4% X-gal and 25 μl of isopropyl-1-thio-β-D-galactoside on LB agar medium [1% Bacto-tryptone (Difco Laboratories Inc.), 0.5% yeast extract, 1% sodium chloride, and 1.5% agar] containing 50 μg/ml ampicillin, and spreading the drops on the medium with a spreader, followed by slight drying. After the completion of culturing, the formed white colony was isolated and cultured. A plasmid DNA was extracted and purified from the culture to obtain plasmid pHK179.

About 5 μg of pHK179 plasmid DNA was dissolved in 20 μl of H buffer, and 10 units each of restriction enzymes MluI and SpeI were added thereto. Reaction was carried out at 37° C. for 3 hours. The reaction product was subjected to treatment for making blunt ends by using DNA Blunting Kit (Takara Shuzo Co., Ltd.), followed by separation by 0.8% agarose gel electrophoresis. The segment of the gel containing the band of a fragment of about 10 Kbp excluding the fragment of about 0.6 kb from MluI (the sequence at positions 4388 through 4393 in SEQ ID NO: 1) to SpeI (the sequence at positions 5027 through 5032 in SEQ ID NO: 1) shown in FIG. 1 was cut out, and the fragment was extracted and purified by using GENECLEAN II Kit. Separately, about 5 μg of YEp24 plasmid DNA, which is a vector carrying the marker gene URA3 complementing uracil-requirement mutation between the HindIII sites, was dissolved in 20 μl of M buffer [10 mM Tris hydrochloride buffer (pH 7.5), 10 mM magnesium chloride, 1 mM dithiothreitol, and 50 mM sodium chloride]. Ten units of restriction enzyme HindIII was added to the solution, and reaction was carried out at 37° C. for 3 hours. The reaction product was subjected to treatment for making blunt ends by using DNA Blunting Kit (Takara Shuzo Co., Ltd.), followed by separation by 0.8% agarose gel electrophoresis. The segment of the gel containing the band of a fragment of about 1.1 kb carrying URA3 was cut out, and the fragment was extracted and purified by using GENECLEAN II Kit. The DNA fragment of about 10 kb derived from plasmid pHK179 (0.5 μg) and the DNA fragment of about 1.1 kb derived from plasmid YEp24 (0.5 μg) were subjected to ligation reaction overnight at 16° C. using Ligation Pack. The reaction mixture (2 μl) was used for transformation of competent high *E. coli* JM109 strain. The obtained transformant was smeared on LB agar medium containing 50 μg/ml ampicillin and cultured at 37° C. for 20 hours. After the completion of culturing, the formed colony was isolated and cultured. A plasmid DNA was extracted and purified from the culture to obtain plasmid pHK188 for disruption of CSF1 gene. Plasmid pHK188 was confirmed to be the desired plasmid by subjecting the plasmid to 0.8% agarose gel electrophoresis and measuring the molecular weight before and after cleavage of the plasmid with BamHI.

Figure 2:
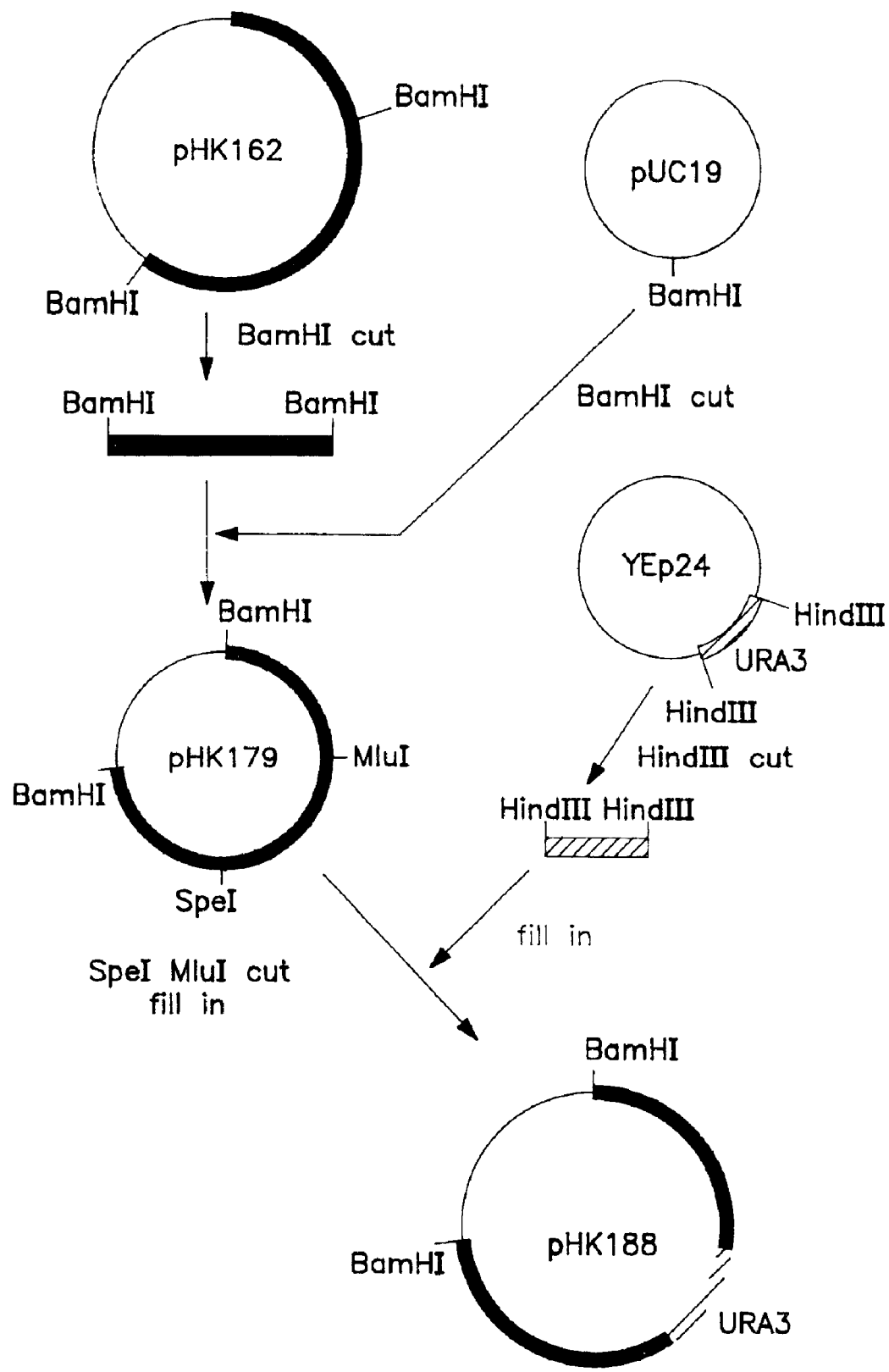
FIG. 2 illustrates the steps for constructing the plasmid for the disruption of CSF1 gene.

The outline of the steps for constructing the plasmid for the disruption of CSF1 gene is shown in FIG. 2.

(2) Disruption of CSF1 Gene

Disruption of CSF1 gene carried by YOY655u strain, which is a monoploid strain of *Saccharomyces cerevisiae*, was carried out by using plasmid pHK188. YOY655u strain is a strain prepared by introducing uracil-requirement (ura3) mutation into YOY655 strain, which is a monoploid strain of *Saccharomyces cerevisiae*. The properties such as fermentability of YOY655u strain are the same as those of YOY655 strain. YOY655u strain was inoculated into 100 ml of YPD medium in an Erlenmeyer flask, and cultured with shaking at 30° C. until the cell density reached 2–4×10$^7$. After the completion of culturing, the cells were collected by centrifugation (2500 rpm, 5 minutes) and then brought into contact with plasmid pHK188 by the lithium acetate method. In order to accelerate the homologous recombination of CSF1 gene with plasmid pHK188, plasmid pHK188 had been linearized by complete digestion with BamHI prior to the transformation. YOY655u strain contacted with plasmid pHK188 was inoculated on SGlu agar medium (0.67% Yeast Nitrogen Base w/o Amino Acid, 2% glucose, and 2% agar), and cultured at 30° C. for 2 to 5 days. After the completion of culturing, YHK1243 strain was obtained from one of the formed colonies as a transformant in which the uracil-requirement of YOY655u strain was complemented.

YHK1243 strain, YOY655u strain and RZT-3 strain were inoculated on YPG agar medium, and cultured at 30° C. for 1 to 2 days to form colonies. Then, a pigment agar was layered over the medium, followed by culturing at 5° C. for 3 days. No color change was observed around the colonies of YHK1243 strain and RZT-3 strain during the culturing, whereas the color around the colony of YOY655u strain changed to yellow on the first day of culturing.

EXAMPLE 3

Process for Making Bread with Refrigerated Dough (1) Culturing of Baker's Yeast

YOY655 strain and YHK1243 strain were respectively cultured in the following manner. That is, one loopful of each strain was inoculated into 30 ml of YPD medium in a 300-ml Erlenmeyer flask, and cultured at 30° C. for 24 hours. The whole of the resulting culture was inoculated into 270 ml of a molasses medium (3% molasses, 0.193% urea, 0.046% potassium dihydrogenphosphate, and 2 drops of defoaming agent) in a 2-l Erlenmeyer flask with baffles, and cultured at 30° C. for 24 hours. After the completion of culturing, the cells were collected by centrifugation and washed twice with deionized water, followed by dehydration on a clay plate. The obtained cells were used for making bread.

(2) Preparation of Bread

Bread was made according to the following dough composition and steps.

| | (weight: g) |
|---|---|
| Dough Composition: | |
| Hard flour | 100 |
| Sugar | 5 |
| Salt | 2 |
| Yeast cells | 2 |
| Water | 62 |
| Steps: | |
| Mixing | (100 rpm, 2 minutes) |
| Dividing | (34.4 g) |
| Storage | (5° C., 7 days) |
| Proofing | (40° C., 90% RH, 75 minutes) |
| Baking | (220° C., 25 minutes) |

The bread obtained using YHK1243 strain as yeast cells had a large volume compared with the bread obtained using YOY655 strain.

EXAMPLE 4

Alcohol Fermentation

Culturing of Yeast and Alcohol Fermentation

YOY655 strain and YHK1243 strain were respectively cultured in the following manner. That is, one loopful of each strain was inoculated into 5 ml of YPD medium in a test tube, and cultured at 30° C. for 24 hours. After the completion of culturing, 2 ml of the culture was inoculated into 20 ml of a molasses medium (25% molasses and 0.2% ammonium sulfate) in a large test tube, followed by culturing at 37° C. Samples of the culture (0.5 ml each) were taken 16 hours and 40 hours after the start of culturing and analyzed for ethanol concentration.

The results are shown in Table 3.

TABLE 3

| | Ethanol production (%) | |
|---|---|---|
| Culturing Time | YOY655 strain | YHK1243 strain |
| 16 hours | 4.92* | 5.37* |
| 40 hours | 10.8* | 11.2* |

*The difference was significant at the 5% level of significance.

As shown in Table 3, a Large amount of ethanol was produced at 37° C. by the use of YHK1243 strain compared with YOY655 strain.

Industrial Applicability

The present invention provides a protein and a gene which complement the mutation exhibiting low-temperature-sensitive fermentability, refrigeration-resistant yeast which is obtained by inactivation of said gene, and processes for producing bread and ethanol using said yeast.

What is claimed is:

1. Yeast belonging to the genus *Saccharomyces* and having low-temperature-sensitive fermentability in which the gene according to (a) or (b) below is inactivated
   (a) a gene encoding a protein having the amino acid sequence of SEQ ID NO: 2, or
   (b) a gene comprising DNA having the nucleotide sequence of SEQ ID NO: 1.

2. The yeast according to claim 1, wherein the yeast belongs to *Saccharomyces cerevisiae*.

3. The yeast according to claim 1, wherein the sequence at positions 4388 through 7885 in SEQ ID NO: 1 is disrupted.

4. *Saccharomyces cerevisiae* YHK1243 (FERM BP-5327).

5. Dough containing the yeast according to claim 1.

6. A process for making bread which comprises adding the yeast according to claim 1 to dough.

7. A process for producing ethanol which comprises culturing the yeast according to claim 1 in a medium, allowing ethanol to accumulate in the culture, and recovering ethanol from the culture.

8. The yeast according to claim 2, wherein the sequence at positions 4388 through 7885 in SEQ ID NO: 1 is disrupted.

9. Dough containing the yeast according to claim 8.

10. A process for making bread which comprises adding the yeast according to claim 8 to dough.

11. A process for producing ethanol which comprises culturing the yeast according to claim 8 in a medium, allowing ethanol to accumulate in the culture, and recovering ethanol from the culture.

* * * * *

UNITED STATES PATENT AND TRADEMARK OFFICE
CERTIFICATE OF CORRECTION

PATENT NO.     : 6,924,132 B1
DATED          : August 2, 2005
INVENTOR(S)    : Kawasaki et al.

It is certified that error appears in the above-identified patent and that said Letters Patent is hereby corrected as shown below:

Title page,
Item [75], Inventors, "Masaya Tokai, Setagaya-ku (JP);" should read -- Masaya Tokai, Tokyo (JP); --.
Item [30], Foreign Application Priority Data, "Dec. 28, 1995 (JP) … 7/343700" should read -- Dec. 28, 1995 (JP) ….. 7-343700 --.

Column 1,
Line 47, "flocoulation" should read -- flocculation --.

Column 3,
Line 8, "Saccharomvces" should read -- Saccharomyces --.

Column 8,
Line 37, "at 5" should read -- at 25 --.

Column 10,
Line 6, "YCP50" should read -- YCp50 --;
Line 43, "Sau3AI/3amHI-BamHI" should read -- Sau3AI/BamHI-BamHI --.

Column 14,
Line 33, "Large" should read -- large --.

UNITED STATES PATENT AND TRADEMARK OFFICE
CERTIFICATE OF CORRECTION

PATENT NO. : 6,924,132 B1
DATED : August 2, 2005
INVENTOR(S) : Kawasaki et al.

It is certified that error appears in the above-identified patent and that said Letters Patent is hereby corrected as shown below:

<u>Column 15,</u>
Line 13, "Location: 5027" should read -- Location: 5927 --.

<u>Column 17,</u>
Line 57, "TTT GGC TAC AAT GAC TTG GAA AAT ATA TTA TTA TAT GAC ACT GAG ACG 2976" should read -- TTT GGC TAC AAT GAC TTG GAA AAT ATA TTA TTA TAT GAC ACT GAG ACC 2976 --.

<u>Column 39,</u>
Line 21, "inactivated" should read -- inactivated: --.

Signed and Sealed this

Twenty-eighth Day of March, 2006

JON W. DUDAS
*Director of the United States Patent and Trademark Office*

```
SEQUENCE LISTING (1) GENERAL INFORMATION:

(iii) NUMBER OF SEQUENCES: 2

(2) INFORMATION FOR SEQ ID NO: 1 :

(i) SEQUENCE CHARACTERISTICS:
        (A) LENGTH: 8874 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Saccharomyces cerevisiae
        (B) STRAIN: X2180-1B (ix) FEATURE:
        (A) NAME/KEY: CDS
        (B) LOCATION: 1 to 8874
        (C) IDENTIFICATION METHOD: E
```

(ix) FEATURE:
            (A) NAME/KEY: cleavage-site
            (B) LOCATION: 1291 to 1296
            (C) IDENTIFICATION METHOD: S (ix) FEATURE:
            (A) NAME/KEY: cleavage-site
            (B) LOCATION: 4388 to 4393
            (C) IDENTIFICATION METHOD: S (ix) FEATURE:
            (A) NAME/KEY: cleavage-site
            (B) LOCATION: 5027 to 5032
            (C) IDENTIFICATION METHOD: S (ix) FEATURE:
            (A) NAME/KEY: cleavage-site
            (B) LOCATION: 7675 to 7680
            (C) IDENTIFICATION METHOD: S (xi) SEQUENCE DESCRIPTION: SEQ ID NO: 1

| | |
|---|---|
| ATG GAA GCT ATT TCA CAA TTA CGT GGT GTT CCA TTG ACA CAC CAA AAG | 48 |
| GAC TTT AGC TGG GTC TTT TTA GTA GAT TGG ATT CTC ACG GTA GTA GTA | 96 |
| TGT TTG ACA ATG ATA TTC TAC ATG GGA AGA ATC TAT GCA TAC CTT GTA | 144 |
| AGT TTT ATA TTA GAA TGG CTA CTA TGG AAA CGA GCG AAA ATC AAG ATA | 192 |
| AAT GTT GAG ACA CTT CGT GTC TCC TTA CTA GGT GGT CGA ATA CAT TTT | 240 |
| AAA AAC CTT TCC GTA ATA CAC AAA GAT TAT ACA ATT TCG GTA TTA GAG | 288 |
| GGT AGT TTA ACA TGG AAA TAC TGG CTT TTA AAT TGC AGA AAA GCA GAA | 336 |
| TTG ATA GAG AAT AAC AAG TCT TCT TCT GGC AAA AAA GCA AAG CTT CCC | 384 |
| TGT AAA ATT TCC GTA GAA TGT GAA GGT CTA GAA ATT TTT ATT TAC AAC | 432 |
| AGA ACA GTG GCG TAC GAT AAT GTT ATA AAC TTA CTA TCA AAA GAT GAA | 480 |
| CGC GAT AAA TTT GAA AAA TAC CTT AAT GAG CAT TCT TTT CCT GAA CCT | 528 |
| TTT AGC GAT GGA AGT AGT GCT GAT AAA TTA GAT GAA GAT CTA AGC GAA | 576 |
| TCT GCA TAC ACA ACG AAC TCT GAT GCA TCA ATT GTT AAT GAC AGG GAC | 624 |
| TAC CAA GAA ACA GAT ATC GGC AAA CAT CCA AAG CTA CTG ATG TTT TTA | 672 |
| CCA ATT GAG CTT AAA TTT AGC CGC GGT TCC CTA CTG TTA GGA AAC AAA | 720 |
| TTC ACG CCA TCT GTT ATG ATT CTA AGT TAT GAA AGT GGA AAA GGC ATA | 768 |
| ATA GAT GTT TTA CCT CCA AAA GAG CGA TTA GAT TTA TAC AGA AAT AAA | 816 |
| ACA CAG ATG GAA TTC AAA AAC TTC GAA ATT TCT ATC AAA CAA AAT ATT | 864 |
| GGT TAC GAT GAT GCT ATT GGA TTG AAG TTT AAA ATA GAT AGA GGG AAA | 912 |
| GTG TCA AAG TTA TGG AAA ACG TTT GTA CGA GTC TTT CAG ATA GTA ACC | 960 |
| AAG CCT GTT GTA CCG AAA AAG ACT AAA AAA AGC GCA GGC ACA TCA GAT | 1008 |
| GAC AAT TTC TAT CAT AAA TGG AAA GGT TTA TCT CTT TAT AAG GCT TCT | 1056 |
| GCG GGC GAC GCT AAA GCA AGT GAT TTA GAT GAT GTT GAG TTC GAT TTG | 1104 |
| ACG AAC CAT GAA TAT GCT AAA TTT ACA TCA ATT TTA AAA TGC CCA AAG | 1152 |
| GTC ACA ATT GCA TAT GAC GTG GAT GTT CCG GGC GTT GTG CCA CAT GGT | 1200 |
| GCA CAT CCG ACA ATA CCT GAT ATT GAT GGA CCA GAT GTG GGC AAT AAC | 1248 |
| GGA GCA CCT CCA GAT TTT GCT TTA GAT GTT CAA ATT CAC GGA GGA TCC | 1296 |
| ATC TGT TAC GGA CCT TGG GCT CAA AGA CAA GTC AGT CAT CTA CAA AGA | 1344 |

-continued

| | |
|---|---|
| GTT CTA TCA CCG GTA GTT TCA AGG ACA GCC AAA CCT ATA AAA AAA CTC | 1392 |
| CCG CCA GGT TCT AGA AGA ATA TAT ACA CTT TTC AGG ATG AAT ATA TCA | 1440 |
| ATA ATG GAA GAT ACT ACT TGG CGT ATA CCG ACG AGG GAA AGT AGC AAA | 1488 |
| GAC CCC GAA TTT TTG AAA CAC TAC AAA GAA ACT AAT GAA GAA TAT AGG | 1536 |
| CCA TTT GGA TGG ATG GAT CTC CGA TTT TGT AAG GAC ACC TAT GCA AAT | 1584 |
| TTC AAT ATA AGT GTT TGT CCT ACA GTG CAA GGT TTT CAG AAT AAT TTC | 1632 |
| CAT GTT CAT TTC CTG GAA ACC GAA ATT AGG TCA AGT GTT AAT CAC GAT | 1680 |
| ATT TTG TTA AAA AGC AAG GTA TTC GAT ATT GAT GGG GAT ATT GGA TAT | 1728 |
| CCA TTG GGT TGG AAT AGC AAA GCT ATA TGG ATA ATT AAC ATG AAG TCA | 1776 |
| GAA CAA TTA GAG GCG TTT CTG CTA CGT GAG CAT ATA ACT TTA GTT GCA | 1824 |
| GAT ACG CTT TCA GAC TTT TCC GCT GGT GAT CCT ACG CCT TAC GAA CTT | 1872 |
| TTT AGA CCA TTC GTA TAC AAA GTC AAT TGG GAA ATG GAA GGA TAT TCC | 1920 |
| ATT TAC TTA AAC GTC AAT GAT CAC AAT ATT GTT AAC AAT CCG TTA GAT | 1968 |
| TTT AAC GAA AAC TGT TAT TTA TCC CTT CAT GGT GAT AAG CTT TCA ATT | 2016 |
| GAT GTC ACG GTA CCC CGT GAG AGT ATT TTG GGG ACA TAC ACA GAT ATG | 2064 |
| TCC TAC GAG ATC TCA ACT CCA ATG TTC AGA ATG ATG TTA AAT ACC CCC | 2112 |
| CCT TGG AAT ACA TTG AAC GAA TTC ATG AAA CAT AAA GAA GTG GGG AGA | 2160 |
| GCA TAC GAC TTT ACA ATT AAA GGT TCT TAC CTT CTC TAT TCC GAG TTA | 2208 |
| GAT ATT GAT AAT GTC GAT ACG CTA GTC ATA GAG TGT AAC AGC AAG AGT | 2256 |
| ACA GTA CTT CAC TGC TAT GGG TTT GTC ATG AGG TAT TTA ACA AAC GTA | 2304 |
| AAG ATG AAT TAC TTC GGT GAA TTT TTT AAT TTT GTG ACG TCA GAA GAG | 2352 |
| TAC ACA GGT GTC CTT GGC GCT AGG GAA GTC GGA GAT GTC ACT ACG AAA | 2400 |
| AGC TCG GTG GCA GAT TTG GCA TCT ACT GTA GAT TCA GGG TAC CAA AAT | 2448 |
| AGC AGT CTA AAG AAC GAA TCT GAG GAT AAA GGT CCT ATG AAA AGG TCA | 2496 |
| GAT TTG AAA AGG ACT ACC AAC GAA ACT GAT ATT TGG TTC ACA TTT TCG | 2544 |
| GTT TGG GAT GGT GCT CTG ATA TTA CCA GAA ACG ATT TAC AGT TTT GAT | 2592 |
| CCA TGC ATT GCA CTA CAT TTT GCC GAA CTT GTA GTG GAT TTC AGA AGT | 2640 |
| TGT AAT TAT TAT ATG GAC ATA ATG GCG GTT CTC AAC GGG ACT TCA ATA | 2688 |
| AAG CGG CAC GTT TCA AAA CAA ATA AAT GAA GTA TTT GAT TTT ATA CGT | 2736 |
| CGT AAT AAC GGA GCT GAT GAG CAA GAG CAC GGA TTG CTT TCG GAC CTC | 2784 |
| ACC ATT CAT GGA CAT AGA ATG TAT GGA TTA CCA CCC ACA GAA CCT ACC | 2832 |
| TAC TTT TGT CAA TGG GAT ATC AAT CTC GGA GAT TTA TGC ATT GAT TCA | 2880 |
| GAT ATT GAA TTT ATA AAG GGA TTC TTT AAT TCC TTT TAT AAG ATA GGT | 2928 |
| TTT GGC TAC AAT GAC TTG GAA AAT ATA TTA TTA TAT GAC ACT GAG ACG | 2976 |
| ATT AAT GAT ATG ACC TCG CTA ACC GTG CAC GTT GAA AAA ATA AGA ATA | 3024 |
| GGC CTT AAA GAT CCG GTG ATG AAA TCT CAA TCA GTT ATT AGT GCT GAA | 3072 |
| TCG ATA TTG TTT ACT TTG ATC GAC TTT GAA AAC GAA AAA TAT TCA CAA | 3120 |
| AGA ATA GAC GTG AAA ATT CCA AAA TTG ACA ATT CGT TAA ATT GCG TG | 3168 |
| ATG GGC GAT GGC GTA GAC ACA TCA TTT CTC AAA TTC GAA ACA AAA TTA | 3216 |
| AGA TTT ACA AAC TTT GAG CAA TAC AAG GAT ATC GAT AAA AAA AGA TCA | 3264 |

-continued

```
GAA CAA CGC AGA TAT ATA ACA ATA CAC GAT TCA CCC TAT CAT AGG TGT      3312
CCT TTT CTT CTT CCG CTG TTC TAT CAG GAT TCG GAT ACA TAC CAA AAC      3360
CTG TAC GGG GCT ATA GCA CCA TCT TCG TCT ATC CCA ACT TTA CCT CTT      3408
CCC ACT TTG CCT GAT ACT ATA GAT TAT ATC ATT GAA GAT ATT GTG GGC      3456
GAG TAT GCT ACC CTT CTG GAG ACC ACA AAT CCA TTC AAG AAC ATA TTC      3504
GCA GAA ACT CCA TCA ACT ATG GAG CCT TCA AGA GCC AGC TTC AGT GAA      3552
GAT GAT AAT GAC GAA GAA GCG GAC CCT TCA AGC TTC AAA CCT GTC GCT      3600
TTT ACA GAA GAC AGA AAC CAC GAA AGG GAT AAC TAT GTT GTT GAT GTT      3648
TCA TAT ATT CTG TTG GAT GTC GAC CCG TTG CTT TTT ATT TTC GCT AAG      3696
AGT TTA TTA GAA CAG CTT TAC TCT GAA AAC ATG GTA CAA GTC TTA GAC      3744
GAT ATT GAA ATT GGG ATT GTG AAA CGA TTA AGC AAC CTT CAA GAA GGG      3792
ATC ACT TCT ATT TCA AAC ATT GAT ATC CAT ATT GCT TAT CTA AAT TTA      3840
ATC TGG CAA GAG ACA GGT GAG GAA GGT TTT GAG CTC TAT TTA GAT CGT      3888
ATT GAT TAT CAA ATG AGT GAA AAG TCT CTA GAG AAG AAC CGA ACA AAT      3936
AAA TTA TTA GAA GTA GCA GCT TTA GCA AAG GTA AAA ACT GTC AGA GTG      3984
ACT GTT AAC CAG AAG AAA AAT CCA GAC TTG TCT GAA GAT CGT CCC CCT      4032
GCA CTG TCG CTA GGG ATT GAG GGT TTC GAA GTA TGG TCT TCT ACA GAA      4080
GAT AGA CAA GTT AAC TCA TTA AAC TTA ACG TCA TCA GAT ATT ACC ATA      4128
GAC GAA TCT CAA ATG GAA TGG CTG TTT GAG TAC TGT AGT GAC CAG GGA      4176
AAT CTT ATT CAA GAG GTT TGC ACT TCT TTT AAT TCT ATT CAG AAC ACC      4224
AGA AGT AAT TCA AAG ACA GAA CTC ATT TCA AAG CTC ACA GCC GCA AGC      4272
GAA TAT TAT CAA ATT AGT CAT GAT CCT TAC GTC ATA ACA AAA CCT GCT      4320
TTT ATT ATG AGA CTT TCC AAA GGG CAT GTG CGT GAG AAT CGT AGT TGG      4368
AAA ATT ATT ACG CGT CTG AGA CAC ATT TTA ACG TAC CTT CCT GAT GAT      4416
TGG CAA AGC AAC ATC GAC GAA GTG CTA AAA GAA AAG AAA TAT ACC TCT      4464
GCT AAA GAT GCA AAA AAT ATC TTC ATG TCT GTG TTT TCG ACT TGG AGA      4512
AAT TGG GAG TTC TCA GAT GTT GCA AGG TCG TAT ATA TAC GGC AAA TTA      4560
TTC ACG GCA GAA AAT GAG AAA CAT AAA CAA AAT TTG ATT AAA AAA TTG      4608
TTG AAG TGT ACC ATG GGA TCA TTT TAC CTT ACT GTT TAT GGT GAG GGA      4656
TAT GAG GTT GAG CAT AAT TTT GTT GTT GCG GAT GCC AAT CTG GTA GTG      4704
GAT TTG ACG CCT CCG GTG ACA AGC TTA CCT TCA AAT CGA GAA GAA ACT      4752
ATT GAA ATT ACG GGA AGA GTA GGC TCA GTA AAA GGA AAA TTC AGT GAT      4800
AGG TTA CTT AAA TTG CAA GAT CTT ATT CCA CTC ATT GCA GCA GTG GGC      4848
GAA GAT GAC AAA AGT GAT CCA AAA AAG GAG TTA TCA AAG CAA TTC AAA      4896
ATG AAC ACC GTT TTA TTA GTG GAT AAA AGT GAA CTG CAA CTG GTC ATG      4944
GAC CAA ACG AAG CTG ATG AGT AGA ACA GTT GGG GGT AGA GTT AGT TTA      4992
CTA TGG GAA AAT CTA AAA GAT TCA ACT AGT CAA GCG GGT TCA TTG GTT      5040
ATA TTT TCC CAG AAA TCG GAA GTG TGG TTA AAA CAC ACA TCT GTC ATT      5088
TTG GGA GAA GCT CAA CTG CGC GAC TTT TCA GTT TTA GCG ACT ACT GAG      5136
```

-continued

```
GCA TGG TCA CAC AAG CCT ACG ATT CTG ATA AAC AAC CAG TGC GCA GAT      5184
CTT CAT TTT AGA GCA ATG AGT TCA ACT GAG CAA TTA GTA ACC GCT ATT      5232
ACT GAA ATT AGG GAA AGT CTG ATG ATG ATT AAA GAG CGC ATA AAG TTT      5280
AAA CCT AAA TCA AAG AAA AAG TCC CAA TTT GTC GAC CAG AAA ATT AAT      5328
ACA GTC TTG TCA TGT TAT TTT TCA AAC GTT AGT TCT GAA GTT ATG CCG      5376
CTC TCG CCA TTT TAT ATT CGT CAC GAA GCC AAG CAG CTT GAT ATA TAT      5424
TTT AAC AAA TTC GGT TCA AAT GAG ATT TTG TTA AGC ATA TGG GAT ACT      5472
GAT TTT TTC ATG ACA TCG CAC CAG ACA AAG GAG CAA TAC CTA AGG TTT      5520
TCA TTT GGC GAT ATT GAA ATT AAA GGA GGA ATT TCT AGA GAA GGC TAT      5568
TCG TTG ATA AAC GTT GAC ATC TCA ATA TCT ATG ATT AAG TTA ACC TTT      5616
TCG GAG CCG CGC CGT ATT GTA AAC AGT TTT TTA CAA GAT GAA AAG CTT      5664
GCT TCT CAG GGT ATC AAT CTG TTA TAT TCC CTG AAG CCT TTA TTC TTT      5712
AGT TCA AAT CTA CCA AAA AAA GAG AAG CAG GCA CCC TCG ATA ATG ATA      5760
AAT TGG ACA TTA GAT ACT AGC ATT ACT TAT TTT GGT GTT CTT GTG CCA      5808
GTG GCT TCC ACG TAT TTC GTG TTT GAA TTA CAT ATG CTG CTA CTT TCT      5856
CTG ACC AAT ACG AAT AAC GGT ATG TTA CCA GAA GAA ACC AAG GTG ACG      5904
GGA CAG TTT TCC ATC GAA AAC ATC CTA TTT CTA ATA AAG GAG CGG TCA      5952
CTA CCC ATT GGT CTT TCC AAA TTA CTC GAC TTT TCC ATA AAA GTA TCA      6000
ACC CTA CAA AGA ACG GTT GAT ACG GAG CAG TCA TTC CAA GTG GAA AGT      6048
TCT CAT TTC AGG GTC TGC TTA TCT CCT GAT TCT CTA TTA AGA TTA ATG      6096
TGG GGC GCG CAT AAA TTG CTA GAC TTG AGC CAT TAC TAT TCA AGA CGC      6144
CAT GCC CCT AAT ATT TGG AAC ACT AAG ATG TTC ACC GGT AAA AGT GAT      6192
AAG TCA AAA GAA ATG CCC ATA AAT TTC CGT TCA ATA CAC ATC CTG TCC      6240
TAT AAA TTT TGT ATT GGG TGG ATA TTC CAG TAT GGA GCA GGC TCC AAT      6288
CCT GGG TTA ATG TTA GGT TAT AAC AGA TTG TTT TCA GCA TAT GAA AAG      6336
GAT TTT GGG AAA TTC ACA GTT GTG GAC GCT TTT TTC TCT GTT GCG AAT      6384
GGT AAT ACC TCA AGC ACT TTT TTC TCT GAA GGA AAC GAG AAA GAC AAA      6432
TAT AAT AGA AGT TTC TTG CCA AAC ATG CAA ATA TCC TAC TGG TTC AAA      6480
AGA TGT GGT GAG TTG AAA GAT TGG TTT TTT AGA TTT CAT GGT GAA GCA      6528
CTG GAT GTA AAC TTT GTC CCG TCA TTC ATG GAT GTC ATT GAG TCT ACT      6576
TTA CAA TCC ATG CGA GCA TTT CAA GAG CTG AAA AAG AAC ATT CTG GAT      6624
GTG TCC GAG AGT TTG CGT GCG GAA AAT GAT AAT TCT TAT GCT AGT ACC      6672
AGT GTC GAA AGT GCT TCG AGT AGT TTG GCT CCC TTT CTC GAT AAC ATT      6720
AGA TCT GTT AAC TCA AAT TTC AAG TAT GAC GGT GGT GTA TTT AGG GTT      6768
TAC ACG TAC GAA GAT ATT GAA ACC AAG AGT GAG CCA TCT TTT GAA ATA      6816
AAA AGT CCA GTA GTC ACT ATA AAC TGT ACA TAT AAA CAT GAT GAA GAT      6864
AAA GTT AAG CCA CAT AAA TTC AGA ACA TTA ATC ACT GTC GAC CCA ACG      6912
CAT AAT ACT TTG TAT GCG GGA TGT GCT CCT TTA TTA ATG GAA TTT CT      6960
GAA AGT CTG CAA AAG ATG ATA AAG AAA CAT AGC ACC GAC GAA AAA CCA      7008
AAC TTT ACA AAA CCT TCT TCA CAG AAT GTT GAT TAT AAG CGA CTT TTG      7056
```

-continued

```
GAT CAA TTT GAT GTG GCT GTA AAA CTA ACA TCA GCC AAG CAA CAG CTA        7104
AGT TTG AGC TGT GAA CCA AAA GCT AAG GTT CAG GCA GAT GTT GGA TTT        7152
GAA TCG TTT TTG TTC AGT ATG GCT ACC AAT GAG TTC GAC TCT GAA CAG        7200
CCT TTG GAG TTT TCT TTA ACT CTA GAA CAC ACA AAA GCG TCC ATT AAG        7248
CAC ATA TTT TCA AGA GAA GTA AGT ACG TCC TTT GAA GTT GGT TTC ATG        7296
GAC TTG ACG CTT TTA TTT ACA CAT CCT GAT GTA ATC AGT ATG TAT GGA        7344
ACG GGG TTG GTT TCT GAT CTA AGC GTC TTC TTC AAT GTA AAG CAG CTC        7392
CAG AAC CTG TAT TTA TTC TTG GAC ATA TGG AGG TTC AGT AGC ATT TTA        7440
CAC ACA CGG CCA GTG CAA AGA ACT GTT AAT AAG GAA ATT GAA ATG AGT        7488
TCA TTA ACA TCA ACC AAC TAT GCC GAT GCA GGT ACG GAA ATA CCC TGG        7536
TGC TTT ACA TTA ATT TTT ACA AAT GTT AGC GGA GAC GTT GAT TTG GGT        7584
CCT TCT CTC GGT ATG ATT TCA TTA AGG ACA CAA AGA ACA TGG CTG GCC        7632
ACA GAT CAT TAT AAC GAG AAG CGG CAG TTA CTG CAT GCT TTC ACT GAC        7680
GGT ATT AGC TTG ACA TCA GAA GGT AGA CTG AGT GGT TTA TTT GAA GTT        7728
GCG AAT GCA AGT TGG TTA TCA GAA GTA AAA TGG CCA CCT GAA AAA AGC        7776
AAA AAT ACT CAT CCA TTA GTT TCC ACC TCC CTG AAT ATT GAT GAT ATA        7824
GCG GTA AAG GCT GCT TTT GAT TAT CAT ATG TTC TTA ATC GGC ACT ATA        7872
AGT AAC ATA CAC TTC CAT CTT CAT AAT GAA AAG GAT GCC AAG GGG GTT        7920
CTA CCT GAT TTG CTG CAG GTC TCT TTT TCA TCA GAT GAA ATT ATC CTC        7968
AGC TCT ACT GCA TTA GTT GTA GCA AAT ATA CTG GAT ATC TAC AAC ACC        8016
ATT GTA CGT ATG AGG CAG GAT AAT AAA ATA TCG TAT ATG GAG ACG TTG        8064
AGA GAT TCC AAT CCT GGT GAA TCT AGG CAA CCA ATA TTA TAC AAA GAC        8112
ATT TTA AGA TCG CTG AAA TTA CTC AGA ACT GAT CTC TCG GTG AAT ATC        8160
TCC TCT TCA AAG GTC CAG ATT TCG CCA ATA TCT TTA TTC GAT GTG GAA        8208
GTG TTA GTA ATA AGA ATT GAC AAA GTC TCT ATA CGT TCC GAA ACA CAT        8256
TCG GGG AAA AAA TTA AAG ACA GAT TTG CAA CTA CAA GTT TTA GAT GTT        8304
TCT GCA GCG CTT TCT ACT TCC AAA GAA GAA TTA GAT GAG GAA GTT GGA        8352
GCT TCC ATT GCT ATT GAT GAT TAC ATG CAT TAT GCT TCC AAG ATT GTC        8400
GGT GGT ACT ATC ATT GAT ATT CCA AAA CTT GCT GTT CAT ATG ACA ACT        8448
TTA CAA GAA GAA AAG ACA AAT AAT TTA GAA TAT CTA TTT GCT TGC TCT        8496
TTT TCA GAC AAA ATA TCT GTA AGG TGG AAT CTA GGG CCT GTA GAC TTC        8544
ATA AAG GAA ATG TGG ACT ACA CAT GTC AAA GCA CTG GCA GTT CGT CGA        8592
TCC CAG GTA GCA AAT ATT TCC TTT GGA CAA ACT GAG GAA GAA CTT GAA        8640
GAA TCA ATT AAA AAG GAA GAA GCC GCT TCA AAG TTT AAT TAT ATT GCA        8688
CTA GAA GAA CCG CAG ATC GAA GTG CCT CAG ATA AGA GAT CTG GGA GAC        8736
GCC ACT CCA CCT ATG GAA TGG TTT GGT GTC AAT AGA AAA AAA TTT CCG        8784
AAA TTC ACT CAC CAA ACC GCA GTT ATC CCC GTC CAA AAG CTT GTT TAT        8832
CTT GCA GAA AAG CAG TAT GTC AAG ATA CTA GAT GAT ACG CAT              8874
```

(2) INFORMATION FOR SEQ ID NO: 2 :

```
        (i) SEQUENCE CHARACTERISTICS:
            (A) LENGTH: 2958 amino acids
            (B) TYPE: amino acid
            (D) TOPOLOGY: linear (ii) MOLECULE TYPE: protein (vi) ORIGINAL SOURCE:
            (A) ORGANISM: Saccharomyces cerevisiae
            (B) STRAIN: X2180-1B (xi) SEQUENCE DESCRIPTION: SEQ ID NO: 2

Met Glu Ala Ile Ser Gln Leu Arg Gly Val Pro Leu Thr His Gln Lys
1               5                   10                  15

Asp Phe Ser Trp Val Phe Leu Val Asp Trp Ile Leu Thr Val Val Val
                20                  25                  30

Cys Leu Thr Met Ile Phe Tyr Met Gly Arg Ile Tyr Ala Tyr Leu Val
                35                  40                  45

Ser Phe Ile Leu Glu Trp Leu Trp Lys Arg Ala Lys Ile Lys Ile
50                  55                  60

Asn Val Glu Thr Leu Arg Val Ser Leu Leu Gly Arg Ile His Phe
65                  70                  75                  80

Lys Asn Leu Ser Val Ile His Lys Asp Tyr Thr Ile Ser Val Leu Glu
                85                  90                  95

Gly Ser Leu Thr Trp Lys Tyr Trp Leu Leu Asn Cys Arg Lys Ala Glu
                100                 105                 110

Leu Ile Glu Asn Asn Lys Ser Ser Ser Gly Lys Lys Ala Lys Leu Pro
                115                 120                 125

Cys Lys Ile Ser Val Glu Cys Glu Gly Leu Glu Ile Phe Ile Tyr Asn
130                 135                 140

Arg Thr Val Ala Tyr Asp Asn Val Ile Asn Leu Leu Ser Lys Asp Glu
145                 150                 155                 160

Arg Asp Lys Phe Glu Lys Tyr Leu Asn Glu His Ser Phe Pro Glu Pro
                165                 170                 175

Phe Ser Asp Gly Ser Ser Ala Asp Lys Leu Asp Glu Asp Leu Ser Glu
                180                 185                 190

Ser Ala Tyr Thr Thr Asn Ser Asp Ala Ser Ile Val Asn Asp Arg Asp
                195                 200                 205

Tyr Gln Glu Thr Asp Ile Gly Lys His Pro Lys Leu Leu Met Phe Leu
                210                 215                 220

Pro Ile Glu Leu Lys Phe Ser Arg Gly Ser Leu Leu Leu Gly Asn Lys
225                 230                 235                 240

Phe Thr Pro Ser Val Met Ile Leu Ser Tyr Glu Ser Gly Lys Gly Ile
                245                 250                 255

Ile Asp Val Leu Pro Pro Lys Glu Arg Leu Asp Leu Tyr Arg Asn Lys
                260                 265                 270

Thr Gln Met Glu Phe Lys Asn Phe Glu Ile Ser Ile Lys Gln Asn Ile
                275                 280                 285

Gly Tyr Asp Asp Ala Ile Gly Leu Lys Phe Lys Ile Asp Arg Gly Lys
                290                 295                 300

Val Ser Lys Leu Trp Lys Thr Phe Val Arg Val Phe Gln Ile Val Thr
305                 310                 315                 320

Lys Pro Val Val Pro Lys Lys Thr Lys Ser Ala Gly Thr Ser Asp
                325                 330                 335

Asp Asn Phe Tyr His Lys Trp Lys Gly Leu Ser Leu Tyr Lys Ala Ser
                340                 345                 350
```

-continued

```
Ala Gly Asp Ala Lys Ala Ser Asp Leu Asp Asp Val Glu Phe Asp Leu
            355                 360                 365
Thr Asn His Glu Tyr Ala Lys Phe Thr Ser Ile Leu Lys Cys Pro Lys
        370                 375                 380
Val Thr Ile Ala Tyr Asp Val Asp Val Pro Gly Val Val Pro His Gly
385                 390                 395                 400
Ala His Pro Thr Ile Pro Asp Ile Asp Gly Pro Asp Val Gly Asn Asn
                405                 410                 415
Gly Ala Pro Pro Asp Phe Ala Leu Asp Val Gln Ile His Gly Gly Ser
            420                 425                 430
Ile Cys Tyr Gly Pro Trp Ala Gln Arg Gln Val Ser His Leu Gln Arg
        435                 440                 445
Val Leu Ser Pro Val Val Ser Arg Thr Ala Lys Pro Ile Lys Lys Leu
    450                 455                 460
Pro Pro Gly Ser Arg Arg Ile Tyr Thr Leu Phe Arg Met Asn Ile Ser
465                 470                 475                 480
Ile Met Glu Asp Thr Thr Trp Arg Ile Pro Thr Arg Glu Ser Ser Lys
                485                 490                 495
Asp Pro Glu Phe Leu Lys His Tyr Lys Glu Thr Asn Glu Glu Tyr Arg
            500                 505                 510
Pro Phe Gly Trp Met Asp Leu Arg Phe Cys Lys Asp Thr Tyr Ala Asn
        515                 520                 525
Phe Asn Ile Ser Val Cys Pro Thr Val Gln Gly Phe Gln Asn Asn Phe
    530                 535                 540
His Val His Phe Leu Glu Thr Glu Ile Arg Ser Ser Val Asn His Asp
545                 550                 555                 560
Ile Leu Leu Lys Ser Lys Val Phe Asp Ile Asp Gly Asp Ile Gly Tyr
                565                 570                 575
Pro Leu Gly Trp Asn Ser Lys Ala Ile Trp Ile Ile Asn Met Lys Ser
            580                 585                 590
Glu Gln Leu Glu Ala Phe Leu Leu Arg Glu His Ile Thr Leu Val Ala
        595                 600                 605
Asp Thr Leu Ser Asp Phe Ser Ala Gly Asp Pro Thr Pro Tyr Glu Leu
    610                 615                 620
Phe Arg Pro Phe Val Tyr Lys Val Asn Trp Met Glu Gly Tyr Ser
625                 630                 635                 640
Ile Tyr Leu Asn Val Asn Asp His Asn Ile Val Asn Asn Pro Leu Asp
                645                 650                 655
Phe Asn Glu Asn Cys Tyr Leu Ser Leu His Gly Asp Lys Leu Ser Ile
            660                 665                 670
Asp Val Thr Val Pro Arg Glu Ser Ile Leu Gly Thr Tyr Thr Asp Met
        675                 680                 685
Ser Tyr Glu Ile Ser Thr Pro Met Phe Arg Met Met Leu Asn Thr Pro
    690                 695                 700
Pro Trp Asn Thr Leu Asn Glu Phe Met Lys His Lys Glu Val Gly Arg
705                 710                 715                 720
Ala Tyr Asp Phe Thr Ile Lys Gly Ser Tyr Leu Leu Tyr Ser Glu Leu
                725                 730                 735
Asp Ile Asp Asn Val Asp Thr Leu Val Ile Glu Cys Asn Ser Lys Ser
            740                 745                 750
Thr Val Leu His Cys Tyr Gly Phe Val Met Arg Tyr Leu Thr Asn Val
        755                 760                 765
```

-continued

```
Lys Met Asn Tyr Phe Gly Glu Phe Asn Phe Val Thr Ser Glu Glu
770                 775                 780

Tyr Thr Gly Val Leu Gly Ala Arg Glu Val Gly Asp Val Thr Lys
785                 790                 795                 800

Ser Ser Val Ala Asp Leu Ala Ser Thr Val Asp Ser Gly Tyr Gln Asn
                805                 810                 815

Ser Ser Leu Lys Asn Glu Ser Glu Asp Lys Gly Pro Met Lys Arg Ser
                820                 825                 830

Asp Leu Lys Arg Thr Thr Asn Glu Thr Asp Ile Trp Phe Thr Phe Ser
                835                 840                 845

Val Trp Asp Gly Ala Leu Ile Leu Pro Glu Thr Ile Tyr Ser Phe Asp
850                 855                 860

Pro Cys Ile Ala Leu His Phe Ala Glu Leu Val Val Asp Phe Arg Ser
865                 870                 875                 880

Cys Asn Tyr Tyr Met Asp Ile Met Ala Val Leu Asn Gly Thr Ser Ile
                885                 890                 895

Lys Arg His Val Ser Lys Gln Ile Asn Glu Val Phe Asp Phe Ile Arg
                900                 905                 910

Arg Asn Asn Gly Ala Asp Glu Gln Glu His Gly Leu Leu Ser Asp Leu
                915                 920                 925

Thr Ile His Gly His Arg Met Tyr Gly Leu Pro Pro Thr Glu Pro Thr
930                 935                 940

Tyr Phe Cys Gln Trp Asp Ile Asn Leu Gly Asp Leu Cys Ile Asp Ser
945                 950                 955                 960

Asp Ile Glu Phe Ile Lys Gly Phe Phe Asn Ser Phe Tyr Lys Ile Gly
                965                 970                 975

Phe Gly Tyr Asn Asp Leu Glu Asn Ile Leu Leu Tyr Asp Thr Glu Thr
                980                 985                 990

Ile Asn Asp Met Thr Ser Leu Thr Val His Val Glu Lys Ile Arg Ile
                995                 1000                1005

Gly Leu Lys Asp Pro Val Met Lys Ser Gln Ser Val Ile Ser Ala Glu
                1010                1015                1020

Ser Ile Leu Phe Thr Leu Ile Asp Phe Glu Asn Glu Lys Tyr Ser Gln
1025                1030                1035                1040

Arg Ile Asp Val Lys Ile Pro Lys Leu Thr Ile Ser Leu Asn Cys Val
                1045                1050                1055

Met Gly Asp Gly Val Asp Thr Ser Phe Leu Lys Phe Glu Thr Lys Leu
                1060                1065                1070

Arg Phe Thr Asn Phe Glu Gln Tyr Lys Asp Ile Asp Lys Lys Arg Ser
                1075                1080                1085

Glu Gln Arg Arg Tyr Ile Thr Ile His Asp Ser Pro Tyr His Arg Cys
                1090                1095                1100

Pro Phe Leu Leu Pro Leu Phe Tyr Gln Asp Ser Asp Thr Tyr Gln Asn
1105                1110                1115                1120

Leu Tyr Gly Ala Ile Ala Pro Ser Ser Ile Pro Thr Leu Pro Leu
                1125                1130                1135

Pro Thr Leu Pro Asp Thr Ile Asp Tyr Ile Ile Glu Asp Ile Val Gly
                1140                1145                1150

Glu Tyr Ala Thr Leu Leu Glu Thr Thr Asn Pro Phe Lys Asn Ile Phe
                1155                1160                1165

Ala Glu Thr Pro Ser Thr Met Glu Pro Ser Arg Ala Ser Phe Ser Glu
                1170                1175                1180

Asp Asp Asn Asp Glu Glu Ala Asp Pro Ser Ser Phe Lys Pro Val Ala
```

-continued

```
             1185                1190                1195                1200
Phe Thr Glu Asp Arg Asn His Glu Arg Asp Asn Tyr Val Val Asp Val
                 1205                1210                1215
Ser Tyr Ile Leu Leu Asp Val Asp Pro Leu Leu Phe Ile Phe Ala Lys
                 1220                1225                1230
Ser Leu Leu Glu Gln Leu Tyr Ser Glu Asn Met Val Gln Val Leu Asp
                 1235                1240                1245
Asp Ile Glu Ile Gly Ile Val Lys Arg Leu Ser Asn Leu Gln Glu Gly
                 1250                1255                1260
Ile Thr Ser Ile Ser Asn Ile Asp Ile His Ile Ala Tyr Leu Asn Leu
1265                1270                1275                1280
Ile Trp Gln Glu Thr Gly Glu Gly Phe Glu Leu Tyr Leu Asp Arg
                 1285                1290                1295
Ile Asp Tyr Gln Met Ser Glu Lys Ser Leu Glu Lys Asn Arg Thr Asn
                 1300                1305                1310
Lys Leu Leu Glu Val Ala Ala Leu Ala Lys Val Lys Thr Val Arg Val
                 1315                1320                1325
Thr Val Asn Gln Lys Lys Asn Pro Asp Leu Ser Glu Asp Arg Pro Pro
                 1330                1335                1340
Ala Leu Ser Leu Gly Ile Glu Gly Phe Glu Val Trp Ser Ser Thr Glu
1345                1350                1355                1360
Asp Arg Gln Val Asn Ser Leu Asn Leu Thr Ser Ser Asp Ile Thr Ile
                 1365                1370                1375
Asp Glu Ser Gln Met Glu Trp Leu Phe Glu Tyr Cys Ser Asp Gln Gly
                 1380                1385                1390
Asn Leu Ile Gln Glu Val Cys Thr Ser Phe Asn Ser Ile Gln Asn Thr
                 1395                1400                1405
Arg Ser Asn Ser Lys Thr Glu Leu Ile Ser Lys Leu Thr Ala Ala Ser
                 1410                1415                1420
Glu Tyr Tyr Gln Ile Ser His Asp Pro Tyr Val Ile Thr Lys Pro Ala
1425                1430                1435                1440
Phe Ile Met Arg Leu Ser Lys Gly His Val Arg Glu Asn Arg Ser Trp
                 1445                1450                1455
Lys Ile Ile Thr Arg Leu Arg His Ile Leu Thr Tyr Leu Pro Asp Asp
                 1460                1465                1470
Trp Gln Ser Asn Ile Asp Glu Val Leu Lys Glu Lys Lys Tyr Thr Ser
                 1475                1480                1485
Ala Lys Asp Ala Lys Asn Ile Phe Met Ser Val Phe Ser Thr Trp Arg
                 1490                1495                1500
Asn Trp Glu Phe Ser Asp Val Ala Arg Ser Tyr Ile Tyr Gly Lys Leu
1505                1510                1515                1520
Phe Thr Ala Glu Asn Glu Lys His Lys Gln Asn Leu Ile Lys Lys Leu
                 1525                1530                1535
Leu Lys Cys Thr Met Gly Ser Phe Tyr Leu Thr Val Tyr Gly Glu Gly
                 1540                1545                1550
Tyr Glu Val Glu His Asn Phe Val Val Ala Asp Ala Asn Leu Val Val
                 1555                1560                1565
Asp Leu Thr Pro Pro Val Thr Ser Leu Pro Ser Asn Arg Glu Glu Thr
                 1570                1575                1580
Ile Glu Ile Thr Gly Arg Val Gly Ser Val Lys Gly Lys Phe Ser Asp
1585                1590                1595                1600
Arg Leu Leu Lys Leu Gln Asp Leu Ile Pro Leu Ile Ala Ala Val Gly
                 1605                1610                1615
```

```
Glu Asp Asp Lys Ser Asp Pro Lys Lys Glu Leu Ser Lys Gln Phe Lys
            1620                1625                1630

Met Asn Thr Val Leu Leu Val Asp Lys Ser Glu Leu Gln Leu Val Met
        1635                1640                1645

Asp Gln Thr Lys Leu Met Ser Arg Thr Val Gly Gly Arg Val Ser Leu
        1650                1655                1660

Leu Trp Glu Asn Leu Lys Asp Ser Thr Ser Gln Ala Gly Ser Leu Val
1665                1670                1675                1680

Ile Phe Ser Gln Lys Ser Glu Val Trp Leu Lys His Thr Ser Val Ile
            1685                1690                1695

Leu Gly Glu Ala Gln Leu Arg Asp Phe Ser Val Leu Ala Thr Thr Glu
            1700                1705                1710

Ala Trp Ser His Lys Pro Thr Ile Leu Ile Asn Asn Gln Cys Ala Asp
            1715                1720                1725

Leu His Phe Arg Ala Met Ser Ser Thr Glu Gln Leu Val Thr Ala Ile
            1730                1735                1740

Thr Glu Ile Arg Glu Ser Leu Met Met Ile Lys Glu Arg Ile Lys Phe
1745                1750                1755                1760

Lys Pro Lys Ser Lys Lys Lys Ser Gln Phe Val Asp Gln Lys Ile Asn
            1765                1770                1775

Thr Val Leu Ser Cys Tyr Phe Ser Asn Val Ser Ser Glu Val Met Pro
            1780                1785                1790

Leu Ser Pro Phe Tyr Ile Arg His Glu Ala Lys Gln Leu Asp Ile Tyr
            1795                1800                1805

Phe Asn Lys Phe Gly Ser Asn Glu Ile Leu Leu Ser Ile Trp Asp Thr
1810                1815                1820

Asp Phe Phe Met Thr Ser His Gln Thr Lys Glu Gln Tyr Leu Arg Phe
1825                1830                1835                1840

Ser Phe Gly Asp Ile Glu Ile Lys Gly Gly Ile Ser Arg Glu Gly Tyr
            1845                1850                1855

Ser Leu Ile Asn Val Asp Ile Ser Ile Ser Met Ile Lys Leu Thr Phe
            1860                1865                1870

Ser Glu Pro Arg Arg Ile Val Asn Ser Phe Leu Gln Asp Glu Lys Leu
            1875                1880                1885

Ala Ser Gln Gly Ile Asn Leu Leu Tyr Ser Leu Lys Pro Leu Phe Phe
            1890                1895                1900

Ser Ser Asn Leu Pro Lys Lys Glu Lys Gln Ala Pro Ser Ile Met Ile
1905                1910                1915                1920

Asn Trp Thr Leu Asp Thr Ser Ile Thr Tyr Phe Gly Val Leu Val Pro
            1925                1930                1935

Val Ala Ser Thr Tyr Phe Val Phe Glu Leu His Met Leu Leu Leu Ser
            1940                1945                1950

Leu Thr Asn Thr Asn Asn Gly Met Leu Pro Glu Glu Thr Lys Val Thr
            1955                1960                1965

Gly Gln Phe Ser Ile Glu Asn Ile Leu Phe Leu Ile Lys Glu Arg Ser
    1970                1975                1980

Leu Pro Ile Gly Leu Ser Lys Leu Leu Asp Phe Ser Ile Lys Val Ser
1985                1990                1995                2000

Thr Leu Gln Arg Thr Val Asp Thr Glu Gln Ser Phe Gln Val Glu Ser
            2005                2010                2015

Ser His Phe Arg Val Cys Leu Ser Pro Asp Ser Leu Leu Arg Leu Met
            2020                2025                2030
```

-continued

Trp Gly Ala His Lys Leu Leu Asp Leu Ser His Tyr Tyr Ser Arg Arg
        2035                2040                2045

His Ala Pro Asn Ile Trp Asn Thr Lys Met Phe Thr Gly Lys Ser Asp
        2050                2055                2060

Lys Ser Lys Glu Met Pro Ile Asn Phe Arg Ser Ile His Ile Leu Ser
2065                2070                2075                2080

Tyr Lys Phe Cys Ile Gly Trp Ile Phe Gln Tyr Gly Ala Gly Ser Asn
        2085                2090                2095

Pro Gly Leu Met Leu Gly Tyr Asn Arg Leu Phe Ser Ala Tyr Glu Lys
        2100                2105                2110

Asp Phe Gly Lys Phe Thr Val Val Asp Ala Phe Phe Ser Val Ala Asn
        2115                2120                2125

Gly Asn Thr Ser Ser Thr Phe Phe Ser Glu Gly Asn Glu Lys Asp Lys
        2130                2135                2140

Tyr Asn Arg Ser Phe Leu Pro Asn Met Gln Ile Ser Tyr Trp Phe Lys
2145                2150                2155                2160

Arg Cys Gly Glu Leu Lys Asp Trp Phe Phe Arg Phe His Gly Glu Ala
        2165                2170                2175

Leu Asp Val Asn Phe Val Pro Ser Phe Met Asp Val Ile Glu Ser Thr
        2180                2185                2190

Leu Gln Ser Met Arg Ala Phe Gln Glu Leu Lys Lys Asn Ile Leu Asp
        2195                2200                2205

Val Ser Glu Ser Leu Arg Ala Glu Asn Asp Asn Ser Tyr Ala Ser Thr
        2210                2215                2220

Ser Val Glu Ser Ala Ser Ser Leu Ala Pro Phe Leu Asp Asn Ile
2225                2230                2235                2240

Arg Ser Val Asn Ser Asn Phe Lys Tyr Asp Gly Gly Val Phe Arg Val
        2245                2250                2255

Tyr Thr Tyr Glu Asp Ile Glu Thr Lys Ser Glu Pro Ser Phe Glu Ile
        2260                2265                2270

Lys Ser Pro Val Val Thr Ile Asn Cys Thr Tyr Lys His Asp Glu Asp
        2275                2280                2285

Lys Val Lys Pro His Lys Phe Arg Thr Leu Ile Thr Val Asp Pro Thr
        2290                2295                2300

His Asn Thr Leu Tyr Ala Gly Cys Ala Pro Leu Leu Met Glu Phe Ser
2305                2310                2315                2320

Glu Ser Leu Gln Lys Met Ile Lys Lys His Ser Thr Asp Glu Lys Pro
        2325                2330                2335

Asn Phe Thr Lys Pro Ser Ser Gln Asn Val Asp Tyr Lys Arg Leu Leu
        2340                2345                2350

Asp Gln Phe Asp Val Ala Val Lys Leu Thr Ser Ala Lys Gln Gln Leu
        2355                2360                2365

Ser Leu Ser Cys Glu Pro Lys Ala Lys Val Gln Ala Asp Val Gly Phe
        2370                2375                2380

Glu Ser Phe Leu Phe Ser Met Ala Thr Asn Glu Phe Asp Ser Glu Gln
2385                2390                2395                2400

Pro Leu Glu Phe Ser Leu Thr Leu Glu His Thr Lys Ala Ser Ile Lys
        2405                2410                2415

His Ile Phe Ser Arg Glu Val Ser Thr Ser Phe Glu Val Gly Phe Met
        2420                2425                2430

Asp Leu Thr Leu Leu Phe Thr His Pro Asp Val Ile Ser Met Tyr Gly
        2435                2440                2445

Thr Gly Leu Val Ser Asp Leu Ser Val Phe Phe Asn Val Lys Gln Leu

-continued

```
                2450                2455                2460
Gln Asn Leu Tyr Leu Phe Leu Asp Ile Trp Arg Phe Ser Ser Ile Leu
2465                2470                2475                2480
His Thr Arg Pro Val Gln Arg Thr Val Asn Lys Glu Ile Glu Met Ser
                2485                2490                2495
Ser Leu Thr Ser Thr Asn Tyr Ala Asp Ala Gly Thr Glu Ile Pro Trp
                2500                2505                2510
Cys Phe Thr Leu Ile Phe Thr Asn Val Ser Gly Asp Val Asp Leu Gly
                2515                2520                2525
Pro Ser Leu Gly Met Ile Ser Leu Arg Thr Gln Arg Thr Trp Leu Ala
                2530                2535                2540
Thr Asp His Tyr Asn Glu Lys Arg Gln Leu Leu His Ala Phe Thr Asp
2545                2550                2555                2560
Gly Ile Ser Leu Thr Ser Glu Gly Arg Leu Ser Gly Leu Phe Glu Val
                2565                2570                2575
Ala Asn Ala Ser Trp Leu Ser Glu Val Lys Trp Pro Pro Glu Lys Ser
                2580                2585                2590
Lys Asn Thr His Pro Leu Val Ser Thr Ser Leu Asn Ile Asp Asp Ile
                2595                2600                2605
Ala Val Lys Ala Ala Phe Asp Tyr His Met Phe Leu Ile Gly Thr Ile
                2610                2615                2620
Ser Asn Ile His Phe His Leu His Asn Glu Lys Asp Ala Lys Gly Val
2625                2630                2635                2640
Leu Pro Asp Leu Leu Gln Val Ser Phe Ser Ser Asp Glu Ile Ile Leu
                2645                2650                2655
Ser Ser Thr Ala Leu Val Val Ala Asn Ile Leu Asp Ile Tyr Asn Thr
                2660                2665                2670
Ile Val Arg Met Arg Gln Asp Asn Lys Ile Ser Tyr Met Glu Thr Leu
                2675                2680                2685
Arg Asp Ser Asn Pro Gly Glu Ser Arg Gln Pro Ile Leu Tyr Lys Asp
                2690                2695                2700
Ile Leu Arg Ser Leu Lys Leu Leu Arg Thr Asp Leu Ser Val Asn Ile
2705                2710                2715                2720
Ser Ser Ser Lys Val Gln Ile Ser Pro Ile Ser Leu Phe Asp Val Glu
                2725                2730                2735
Val Leu Val Ile Arg Ile Asp Lys Val Ser Ile Arg Ser Glu Thr His
                2740                2745                2750
Ser Gly Lys Lys Leu Lys Thr Asp Leu Gln Leu Gln Val Leu Asp Val
                2755                2760                2765
Ser Ala Ala Leu Ser Thr Ser Lys Glu Glu Leu Asp Glu Glu Val Gly
                2770                2775                2780
Ala Ser Ile Ala Ile Asp Asp Tyr Met His Tyr Ala Ser Lys Ile Val
2785                2790                2795                2800
Gly Gly Thr Ile Ile Asp Ile Pro Lys Leu Ala Val His Met Thr Thr
                2805                2810                2815
Leu Gln Glu Glu Lys Thr Asn Asn Leu Glu Tyr Leu Phe Ala Cys Ser
                2820                2825                2830
Phe Ser Asp Lys Ile Ser Val Arg Trp Asn Leu Gly Pro Val Asp Phe
                2835                2840                2845
Ile Lys Glu Met Trp Thr Thr His Val Lys Ala Leu Ala Val Arg Arg
                2850                2855                2860
Ser Gln Val Ala Asn Ile Ser Phe Gly Gln Thr Glu Glu Glu Leu Glu
2865                2870                2875                2880
```

```
Glu Ser Ile Lys Lys Glu Glu Ala Ala Ser Lys Phe Asn Tyr Ile Ala
            2885                2890                2895

Leu Glu Glu Pro Gln Ile Glu Val Pro Gln Ile Arg Asp Leu Gly Asp
            2900                2905                2910

Ala Thr Pro Pro Met Glu Trp Phe Gly Val Asn Arg Lys Lys Phe Pro
            2915                2920                2925

Lys Phe Thr His Gln Thr Ala Val Ile Pro Val Gln Lys Leu Val Tyr
            2930                2935                2940

Leu Ala Glu Lys Gln Tyr Val Lys Ile Leu Asp Asp Thr His
2945                2950                2955
```